US006685620B2

(12) United States Patent
Gifford, III et al.

(10) Patent No.: US 6,685,620 B2
(45) Date of Patent: Feb. 3, 2004

(54) VENTRICULAR INFARCT ASSIST DEVICE AND METHODS FOR USING IT

(75) Inventors: Hanson S. Gifford, III, Woodside, CA (US); Bernard H. Andreas, Redwood City, CA (US)

(73) Assignee: The Foundry Inc., Redwood City, CA (US)

( * ) Notice: Subject to any disclaimer, the term of this patent is extended or adjusted under 35 U.S.C. 154(b) by 22 days.

(21) Appl. No.: 09/964,070

(22) Filed: Sep. 25, 2001

(65) Prior Publication Data

US 2003/0060674 A1 Mar. 27, 2003

(51) Int. Cl.[7] .................................................. A61F 1/00
(52) U.S. Cl. ............................................ 600/16; 600/37
(58) Field of Search .............................. 600/16, 18, 37; 623/3.1, 3.11; 601/153; 128/897

(56) References Cited

U.S. PATENT DOCUMENTS

| | | | |
|---|---|---|---|
| 3,174,851 A | 3/1965 | Buehler et al. |
| 3,351,463 A | 11/1967 | Rozner et al. |
| 3,753,700 A | 8/1973 | Harrison et al. |
| 5,643,172 A | 7/1997 | Kung et al. |
| 5,702,343 A | 12/1997 | Alferness |
| 5,800,528 A | 9/1998 | Ledermann et al. |
| 5,961,440 A | 10/1999 | Schweich, Jr. et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,077,218 A | 6/2000 | Alferness |
| 6,085,754 A | 7/2000 | Alferness et al. |
| 6,123,662 A | 9/2000 | Alferness et al. |
| 6,126,590 A | 10/2000 | Alferness |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,169,922 B1 | 1/2001 | Alferness et al. |
| 6,174,279 B1 | 1/2001 | Girard |
| 6,183,411 B1 | 2/2001 | Mortier et al. |
| 6,193,648 B1 | 2/2001 | Krueger |
| 6,224,540 B1 | 5/2001 | Lederman et al. |
| 6,230,714 B1 | 5/2001 | Alferness et al. |
| 6,241,654 B1 | 6/2001 | Alferness |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,406,420 B1 * | 6/2002 | McCarthy et al. ............ 600/16 |

OTHER PUBLICATIONS

Jancin, B. (Mar. 15, 2001) "Ventricular Surgery Plus CABG Eyed for Cariomyopathy", *Internal Medicine News* vol. 34(6) pp. 1–2.

* cited by examiner

*Primary Examiner*—Jeffrey R. Jastrazab
(74) *Attorney, Agent, or Firm*—Townsend and Townsend and Crew LLP

(57) ABSTRACT

This relates to surgical devices and methods of using them. In particular, the devices are used to support and to reform myocardial tissue in the region of and across an infarct. The devices provide tension across the infarct in varying degrees by attachment of the device to the myocardium at sites adjacent the infarct. A support-providing component across the infarct, between the heart attachment sites, provides support to the myocardial wall and support across the infarct. Optionally, but preferably, the support-providing component includes a time-delay element that variously may allow the device to be introduced onto the myocardial surface and to change the support of the support element over time.

107 Claims, 13 Drawing Sheets

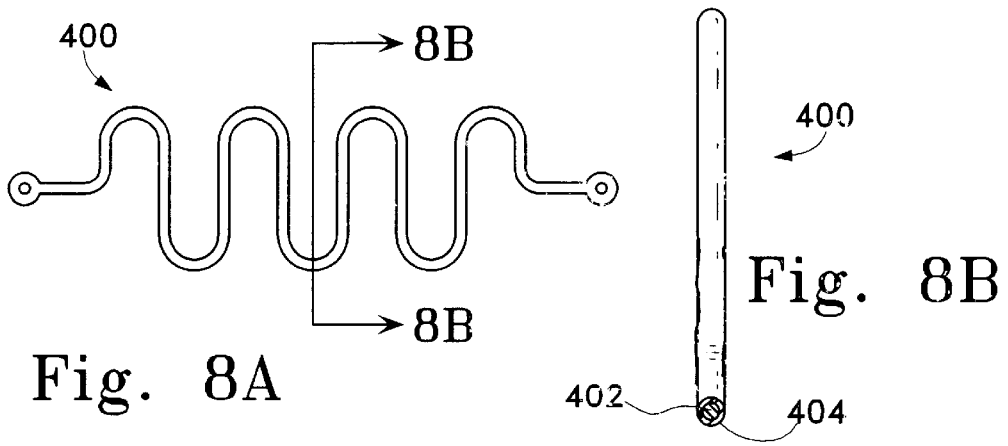
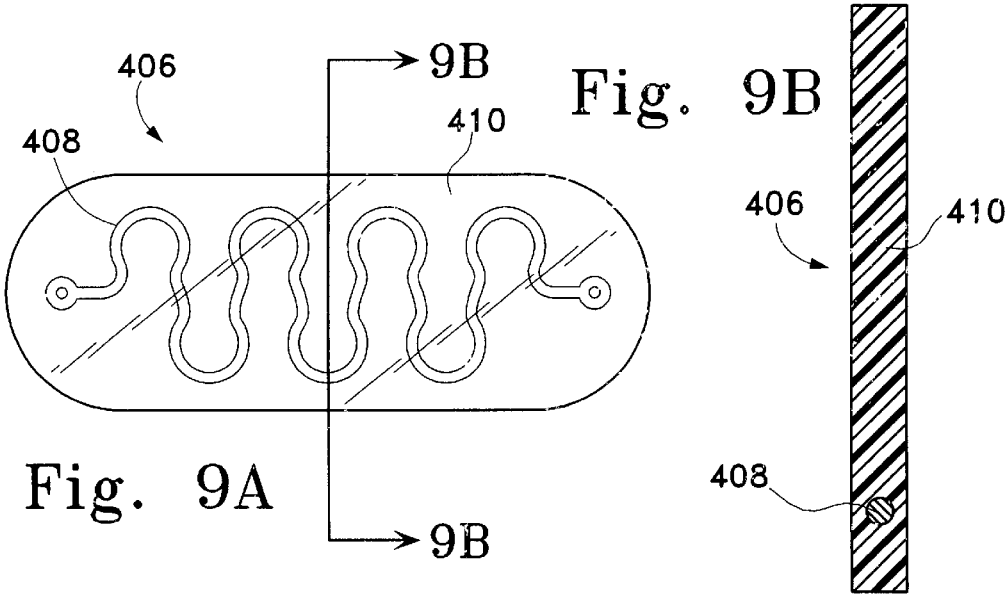
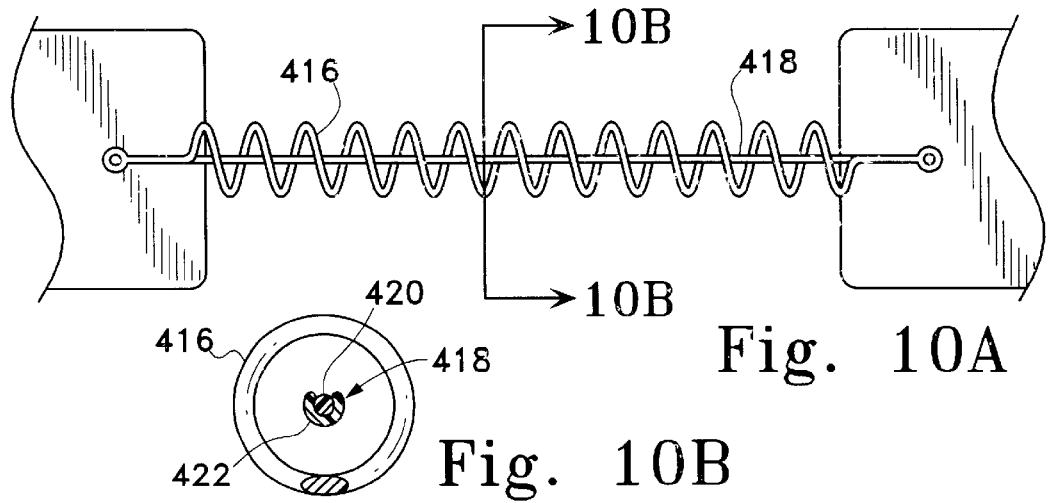

VENTRICULAR INFARCT ASSIST DEVICE AND METHODS FOR USING IT

FIELD OF THE INVENTION

This invention relates to surgical devices and to methods of using them. In particular, the devices are used to support and to reform myocardial tissue in the region of and across an infarct. The devices provide support to the infarct in varying degrees by attachment of the inventive device to the myocardium at sites adjacent the infarct. A supporting component across the infarct, between the heart attachment sites, provides support to the myocardial wall and to the infarcted region. Optionally, but preferably, the supporting component includes a time-delay element that variously may allow the device to be safely manipulated and introduced onto the myocardial surface and then to change the distance between the ends of the support member or the amount of infarct support over time.

BACKGROUND OF THE INVENTION

This invention relates to devices and processes for treating, in particular, ischemic heart diseases, particularly myocardial infarction. The term "myocardial infarction" generally refers to the death of that tissue resulting from either inadequate blood supply or an absolute lack of blood supply to that tissue region. Classically, a "heart attack" occurs with the sudden onset of specific symptoms, followed by a specific series of electrocardiographic changes and a rise in serum levels of enzymes released from the myocardium. Total occlusion of a major coronary artery by thrombosis creates an infarcted area involving virtually the full thickness of the ventricular wall in the region of the heart supplied by the blocked artery. The occlusion of the coronary artery may occur more slowly and not completely block the artery. The resulting infarction then occurs over a significant period of time and may be less localized.

In the United States, myocardial infarction occurs in upwards of two million people a year. Less than half of those persons are hospitalized and a quarter to a third of them die suddenly outside of the hospital.

Coronary artery thrombosis almost always occurs at the site of an atheromatous plaque. Although plaque is present, it does not typically severely narrow the lumen of the affected artery before the thrombosis occurs. The formation of the thrombus is caused by a variety of events and likely may be considered to be the formation of a breakage in the intimal lining or hemorrhage within the plaque. Generally, plaques that are amenable to such fissuring are soft, rich in lipid, and formed in such a way that a fibrous cap overlies the softer lipid material. The fissure frequently occurs at the junction of the fibrous cap and a normal intima. As is a case with any vascular injury of this type, the response is an aggregation of platelets. The platelets begin a cascade of the release of thromboxane, promoting further platelet aggregation, coronary vasoconstriction, further reduction of blood flow, and formation of a thrombus. These coronary occlusions occur without warning signs in most instances, although physical activity and stress may have some role in causation.

In any case, these coronary accidents are easily detectable by electrocardiogram. Similarly, the treatment of acute myocardial infarction is typically via medication. Treatment of pain, perhaps by administering sublingual nitroglycerin is common. The goal of medicinal therapy in such cases is the opening of the partially closed artery. Administration of thrombolytics such as streptokinase, alteplase (recombinant tissue plasminogen activator—rt-PA), and anistreplase (anisoylated plasminogen streptokinase activated complex or APSAC) may be had. In some instances, angioplasty is administered, typically without thrombolysis, but on rare occasions with such a drug.

It is uncommon to treat infarcts with surgery unless there have been anatomic complications of the myocardial infarction, e.g., ventricular septal rupture, mitral regurgitation, ventricular aneurysms, ATC. Two procedures for dealing with myocardial infarcs via surgery are the Batista Procedure and the Dor Procedure, named after the surgeons who first performed them. In the Batista Procedure, the surgeon resects a portion of the heart to change its shape to a more correct cone shape. The Batista Procedure removes both healthy tissue and tissue not so healthy. The procedure is said not to be in favor due to high complication rates.

The Batista Procedure was replaced by a surgery known as the Dor Procedure. The Dor Procedure is less aggressive and apparently more effective. The Dor Procedure is typically used after an aneurysm forms following the presence of an infarct. The Dor Procedure is also called "endoventricular circular patch plasty" or EVCPP. The procedure creates a looped stitch pattern around a dead, scarred aneurysm to shrink the dead area. Any remaining defect may be covered by a patch made from DACRON or tissue. The aneurysm scar is closed over the outside of the patch to make the overall site more stable.

A variation of the Dor Procedure is called the SAVR Procedure, which stands for Surgical Anterior Ventricular Remodeling. This procedure opens the affected ventricle through the "akinetic" segment. A surgeon feels the beating heart and detects, using the fingers, where the heart muscle is not working. A suture is placed at the junction of a beating muscle and non-beating muscle that is typically semicircular, purse-string suture shape. A patch is then installed.

There are a variety of devices which are applied to the heart for treatment of congestive heart failure (CHF). Patents owned by Abiomed (U.S. Pat. Nos. 6,224,540; 5,800,528; 5,643,172) show a girdle-like device situated to provide structure to a failing heart. U.S. patents owned by Acorn Cardiovascular, Inc. (U.S. Pat. Nos. 6,241,654; 6,230,714; 6,193,648; 6,174,279; 6,169,922; 6,165,122; 6,165,121; 6,155,972; 6,126,590; 6,123,662; 6,085,754; 6,077,218; 5,702,343) show various devices, also for treatment of CHF, which typically include a mesh sock-like device placed around the myocardial wall. U.S. patents to Myocor, Inc. (U.S. Pat. Nos. 6,264,602; 6,261,222; 6,260,552; 6,183,411; 6,165,120; 6,165,119; 6,162,168; 6,077,214; 6,059,715; 6,050,936; 6,045,497; 5,961,440) show devices for treatment of CHF generally using components which pierce the ventricular wall.

None of the devices described in any of these patents suggests the devices and methods disclosed here.

SUMMARY OF THE INVENTION

This invention is a heart tissue supporting device comprising a.) at least one first heart tissue adherence region (each adapted to adhere to selected first heart tissue regions on a heart surface), b.) at least one second heart tissue adherence region, separated from the first heart tissue adherence regions and each adapted to adhere to selected second heart tissue regions on a heart surface, and c.) at least one support-providing member situated variously to maintain support to the tissue located between the first heart tissue adherence regions and the second heart tissue adherence regions.

The first and second heart tissue adherence regions may be at least partially surrounded by a region that is substantially non-adhering to heart tissue. The tissue support-maintaining member is sized and placeable to maintain the distance between the first and second heart tissue contact regions. The device may include a connector strap that is substantially non-adhering to heart tissue and is configured to connect the first and second heart tissue adherence regions around the heart not adjacent the infarct to form a loop surrounding the heart. The portions of the device that do not adhere to heart tissue may be made from non-adherent materials such as woven or non-woven polymeric fabrics, e.g., polyfluorocarbons and polyolefins, such as polytetrafluoroethylene (PTFE or TFE), ethylenechlorofluoroethylene (ECTFE), fluorinated ethylene propylene (FEP), polychlorotrifluoroethylene (PCTFE), polyvinylfluoride (PVF), polyvinylidenefluoride (PVDF), polyethylene (LDPE, LLDPE, and HDPE), and polypropylene.

The portions of the device that should adhere to the heart may be made of materials known to adhere, adhering materials selected to allow ingrowth such as woven or non-woven polymeric fabrics desirably selected from polyethyleneterephthalate, cotton, and expanded polyfluorocarbons having internodal spacing suitable for intergrowth.

The device includes at least one support-maintaining member, often having a spring with opposing ends attached between the at least one first heart tissue adherence region and the at least one second heart tissue adherence region. The springs may be coiled or flat or other suitable shape. The support-maintaining member further desirably includes a time-delay member adapted to provide a period of time between the introduction of the device onto the heart and the initiation of a movement of the first heart tissue adherence region towards the second and/or to provide a period of time over which the distance between the first heart tissue adherence region and the second heart tissue adherence region varies.

The time-delay member may be coated with, embedded in, or be formed of a suitable biodegradable material.

The first or second heart tissue adherence regions may have surfaces selected to allow or enhance ingrowth of heart tissue into those regions. The regions may be, e.g., not smooth, roughened, nubbed, perforated, etc.

As appropriate, the surfaces of the device, e.g., the heart tissue supporting member, the time-delay member, and the first and second heart tissue adherence regions, may be treated with at least one angiogenesis composition.

The first and second heart tissue adherence regions may be made to adhere to the heart tissue in a variety of ways, e.g., by mechanical fasteners, by ingrowth, by adhesives, or other materials, devices or procedures that cause the device component to adhere to the heart.

The invention includes methods for use of the device itself, methods of supporting a localized or regional area of a heart particularly where that region includes an infarct or region that has been surgically altered. Procedures typically include the steps of adhering a first tissue contact area of a supporting member to the myocardial wall at a first tissue site adjacent the infarct or other region to be supported, adhering a second tissue contact area of the supporting member to the myocardial wall at a second tissue site adjacent the infarct or other region to be supported but adapted for positioning the supporting member across the region of concern, and maintaining the distance between or advancing the first tissue contact area towards the second tissue contact area. The procedures may involve adhesively connecting the first and second tissue contact areas respectively to first and second tissue sites or by allowing ingrowth or by mechanically fastening a contact area to the tissue site. The step of advancing the two tissue contact area towards each other may take place as a result of the erosion of a bioerodible material situated between those first and second tissue contact areas. The advancing step may comprise eroding a bioerodible material time-delay member associated with the support-maintaining member in such a way that it tends to tend to hold the spring in extension until after functional biodegradation in the human body. The advancing step may include eroding the support-maintaining member itself when that member is made up of a bioerodible material.

Finally, the invention includes a fastener made up of a shaft terminating at one end in a tissue piercing end and having a collar end at the opposite end, a collar slidable on the shaft, and a braided member concentric to the shaft, affixed to the shaft substantially adjacent the tissue piercing end. The fastener operates in the following way. The collar on the on the shaft slides towards the tissue piercing end and expands the braided member. The region between the collar and the braided member is appropriate for fastening. The braided member may be affixed to the collar at the end opposite the tissue piercing end. Desirably, the fastener includes a stop for affixing the shaft to the collar after the braided member has been expanded.

BRIEF DESCRIPTION OF THE DRAWINGS

FIGS. 8A, 9A, and 10A show front views of various supporting members made according to the invention.

FIGS. 8B, 9B, and 10B show cross sections, respectively, of the springs shown in FIGS. 8A, 9A, and 10A.

DESCRIPTION OF THE INVENTION

This invention deals, in general, with devices for supporting and reforming myocardial tissue in the region of and across an infarct. Generally, the device adheres to the myocardial tissue adjacent the infarcted region. The devices also provide support across and to the infarct preferably in a way that varies with time to allow the injured area to reform and generally to allow surrounding tissue to strengthen. In some instances, the tissue may merge opposing areas of substantially healthy myocardial tissue across an infarct location. Used in such a way, the device also prevents resulting injuries such as ventricular aneurysms.

Although the device is preferably introduced onto the heart without removal of the infarcted tissue, the device may also be used after surgical removal of infarcted tissue. The device may be introduced onto the myocardial surface using percutaneous or minimally intrusive procedures. Open chest surgery is also suitable but is not preferred.

Preferably, the inventive device includes a support region generally suitable for placement exteriorly to an infarct that 1.) allows placement of the inventive device onto the heart using selected procedures (e.g., minimally invasive, etc.), and 2.) later (preferably through the use of a temporally biodegradable component) varies the geometry of the support component, e.g., by drawing the ends of the support component together as a function of time, to support the infarcted region and allow reformation of the adjacent myocardial tissue. As noted elsewhere, the ends of the supporting area functionally adhere to healthy myocardial tissue at sites beyond the periphery of the infarcted region.

Figure 1:
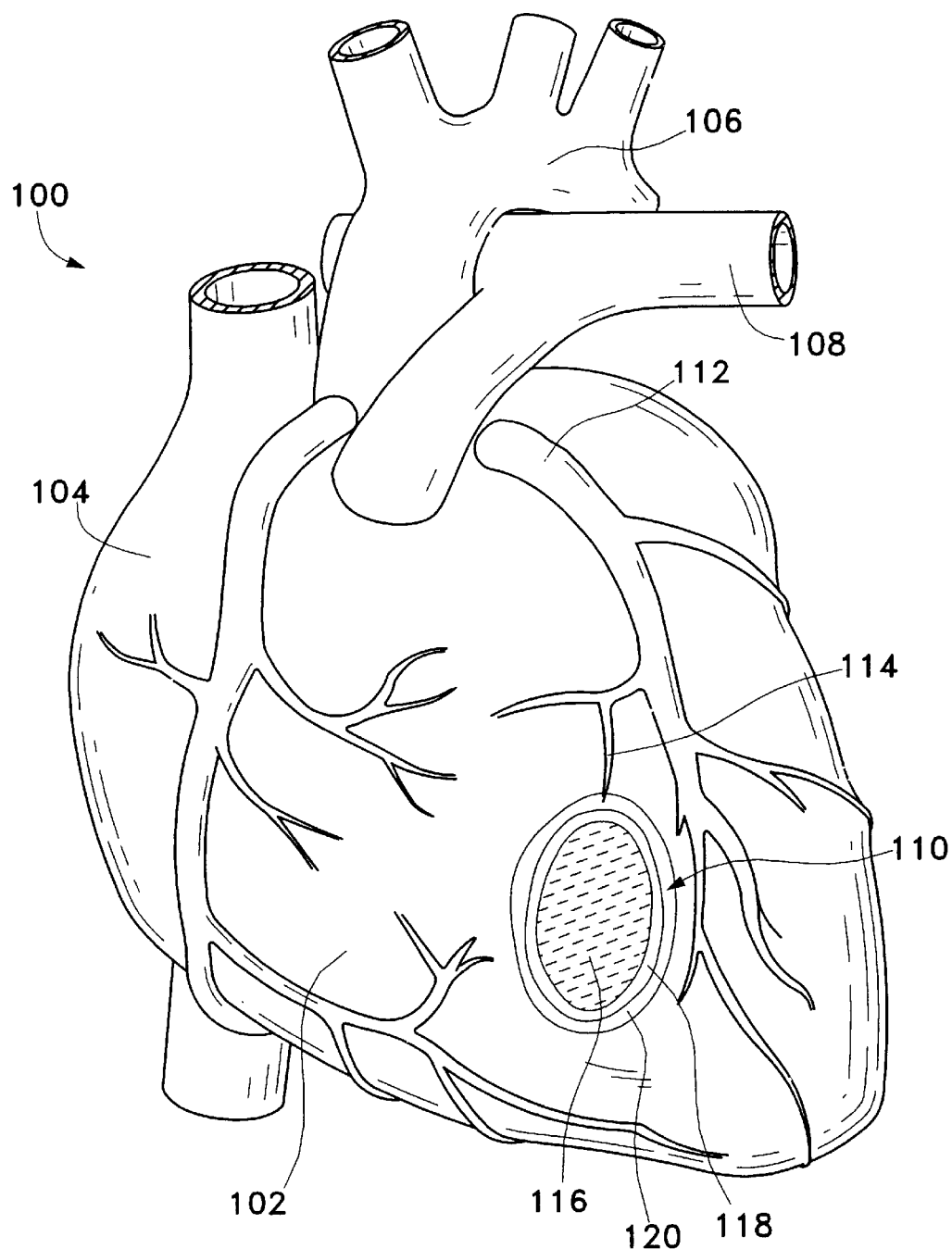
FIG. 1 shows an anterior view of a human heart having a ventricular infarct region.

FIG. 1 shows an anterior view of the heart (100). The right ventricle (102) and right auricle (104) may be seen in this view. The arch of the aorta (106) and pulmonary trunk (108) may also be seen. Also seen from this view is the site of an infarct (110). This injury is typical of those found in the myocardial wall after occlusion of a coronary artery. The infarct (110) shown in this depiction is one that might occur due to the occlusion of some portion of the anterior interventricular branch of the left coronary artery (112). The occlusion typically would reside at or near the site marked (114). The infarct itself generally is considered to have three zones of influence. The first is the zone of infarction (116) and is considered to be simply dead heart muscle tissue. Electrocardial measurements taken over this zone (in a conceptual sense) "see through" the zone of infarction and record electrical activity on the other side of the heart. Surrounding the zone of infarction (116) is the zone of injury (118). Injured cardiac muscle has a cell membrane which is never fully polarized and potentially may be recoverable with the passage of time. Finally, the zone of ischemia (120) surrounds the zone of injury (118). Diagnoses of the scope of these regions is well documented and are determined using electrocardiograms and similar devices.

Figure 2A:
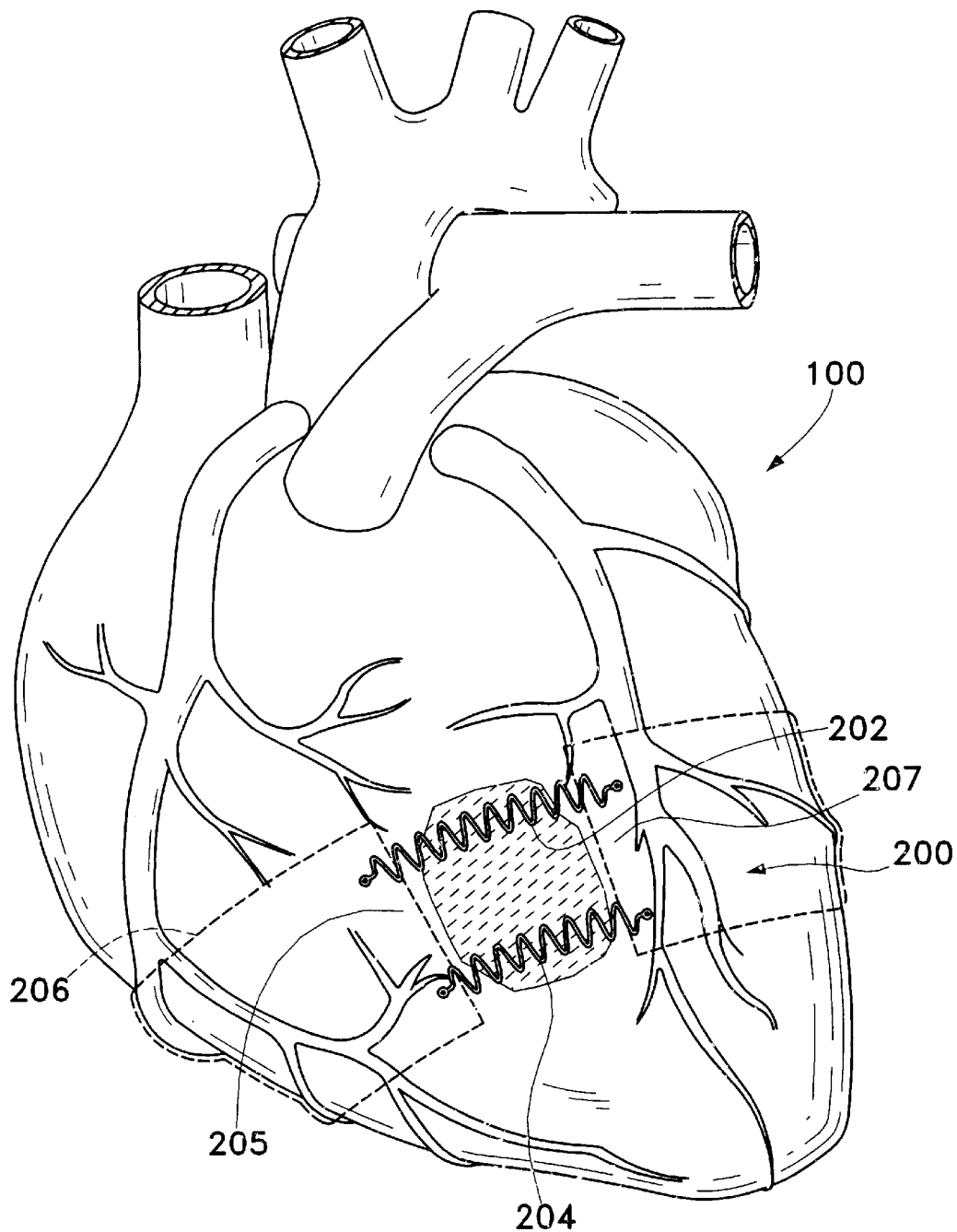
FIGS. 2A and 2B show placement of two variations of the inventive device around an infarcted region. The views are both of an anterior view of the heart.

FIG. 2A depicts, in concept, the desired effect of one variation of the inventive device and a specific procedure for using the device. In particular, schematized inventive device (200) is shown situated about the heart (100). In concept, the device (200) is placed about the infarct (shown in FIG. 1 as (110)) and allowed to adhere to comparatively healthy regions of tissue (205, 207) that are adjacent to the infarct so that upon activation of the device (200), those comparatively healthy regions (205, 207) regions are drawn towards each other thereby tending to shrink the infarct. The springs (202, 204) which act as the support-inducing and -maintaining members across the infarct are also shown. The goal in this variation is to create a region about the infarct in which sufficiently healthy myocardial tissue on one side of the infarct is either 1.) held in a generally static position with respect to sufficiently healthy myocardial tissue on the other side of the infarct and with support for a period of time sufficient to allow wall thickening of some portion of that adjacent tissue and preferably shrinkage of the infarct region and or 2.) moved as a function of time with respect to sufficiently healthy myocardial tissue on the other side of the infarct to reach the same result.

Desirably two or more adherent regions (204) of the inventive device (200) will be put together in such a way that they adhere to the myocardial wall (via mechanical connection or intergrowth with the tissue of the heart). An optional band (206) may be used to maintain position of the inventive device on the selected site.

Figure 2B:
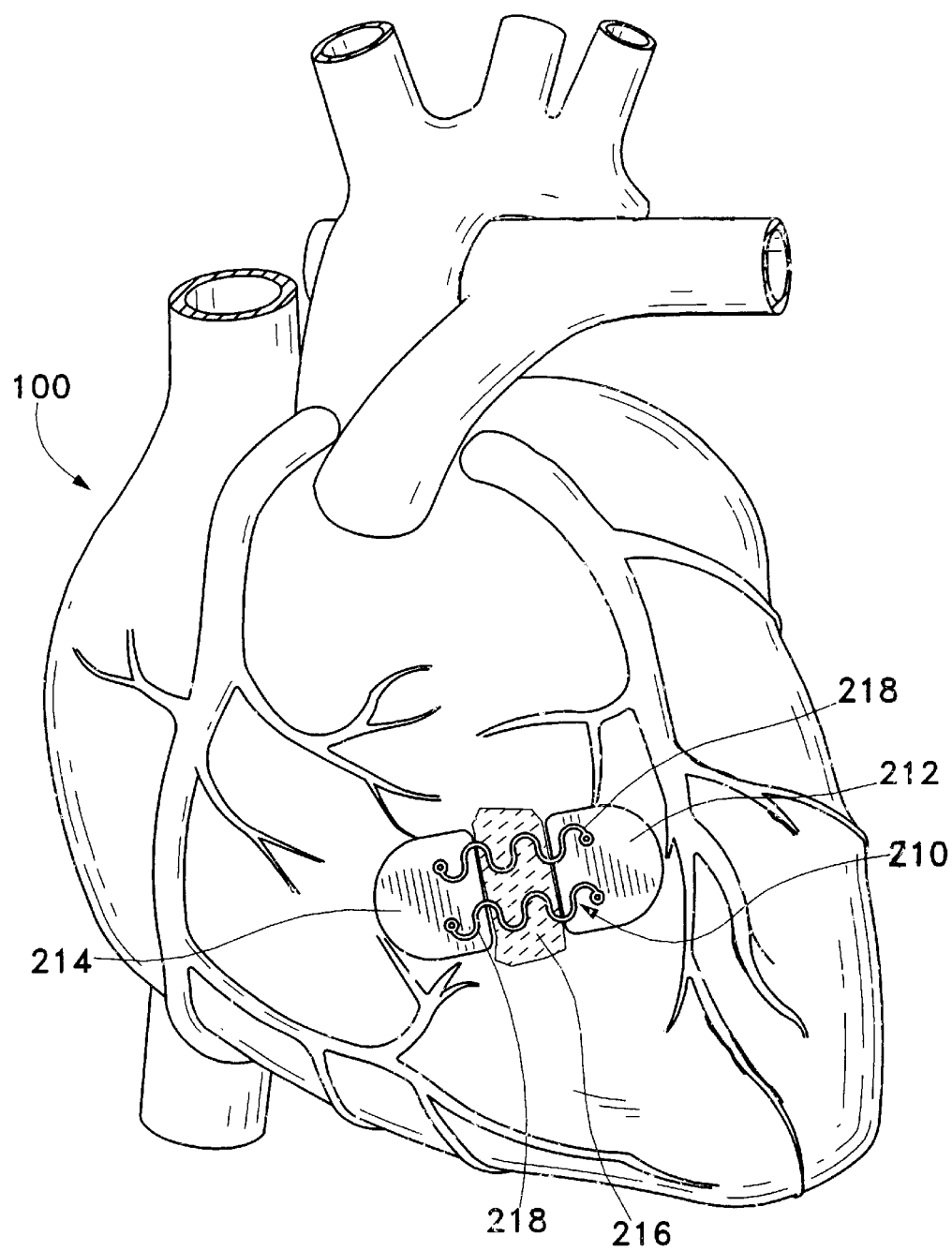

FIG. 2B shows another variation of the inventive device as placed on the ventricular wall of a heart (100). The variation of the inventive device (210) shown in FIG. 2B does not utilize a band about the heart (100) but instead relies on direct adherence of the device sections (212) and (214) to the ventricular surface across the infarct region (216). Adherent regions or portions (212) and (214) may variously be caused to be adherent to the ventricular surface by intergrowth as mentioned above, by a mechanical fastener, as will be discussed below, or by biocompatible adhesives such as cyanoacrylate or fibrin-based glues or by other suitable procedures. Further, the variation shown in FIG. 2B shows the use of flat springs (218) as the support inducing members in device (210). In this variation, springs (218) are coated with a biodegradable or bioabsorbable material which allows the overall distance between the ends of the springs slowly to decrease. As the stiff coating erodes away, the springs themselves decrease in length (end to end) and tend, therefore, to pull the edges of the infarct region (216) towards each other. In this variation of the invention, the device is intended to decrease the distance between the ends over a chosen or specified length of time, allowing reformation of tissue in the infarct regions, support of the ventricular wall, e.g., to prevent ventricular aneurysms.

Figure 3A:
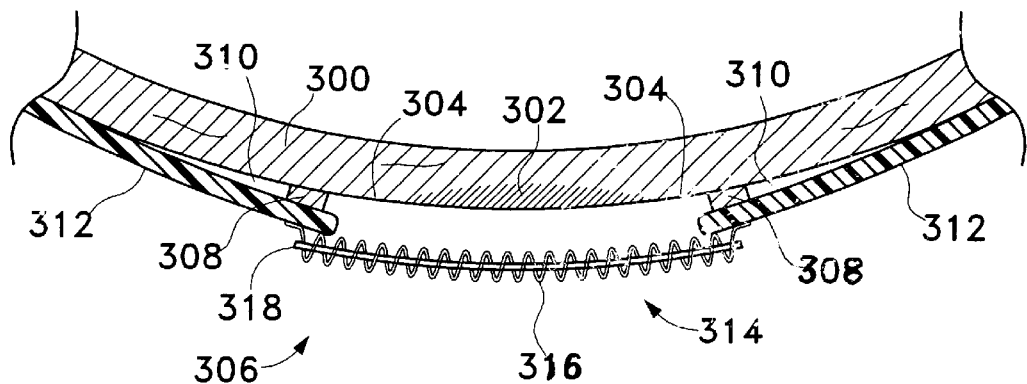
FIGS. 3A, 3B, and 3C show cross-sectional views of a myocardial wall, placement of a variation of the inventive device, and the effect resulting from use of that device.
Figure 3B:
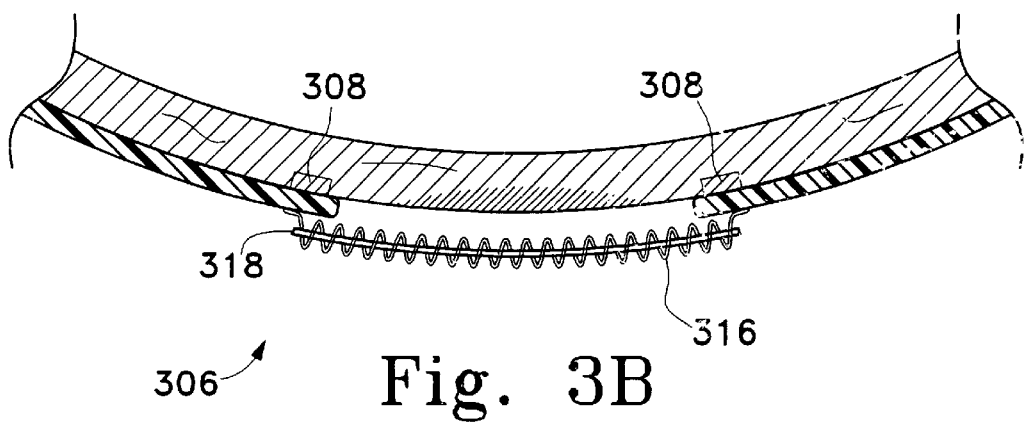
Figure 3C:
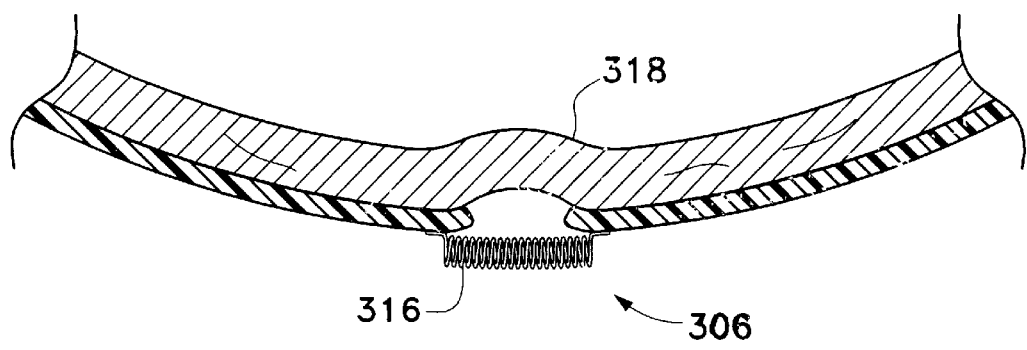

FIGS. 3A, 3B, and 3C show the conceptual operation of the variation of the inventive device as shown in FIG. 2A.

FIG. 3A shows a cross-sectional portion of the myocardial wall (300) and an infarct (302). Peripherally adjacent the infarct (302) are regions (304) of sufficiently healthy myocardial tissue. By "sufficiently healthy" is meant that the tissue is not in the "infarct region" discussed above and will regenerate or reform in time. FIG. 3A shows the inventive device of (306) shortly after its placement on the ventricular wall (300). Included in this schematic depiction are two or more regions (308) that are adapted to adhere to the myocardial wall at about the positions shown in the Figure. Surrounding the adhering regions (308) are regions (310) of the inventive device that generally do not adhere to the heart.

Band (312) is shown in FIG. 3A although other ways of maintaining the inventive device in position until (and after) it is operative are included in the scope of this invention. The support maintaining member (314) is here shown to be made up of a coil spring (316) and a time delay member (318). In function, time delay member (318) may comprise, for instance, a biodegradable plastic which after some period of time erodes to the point where it allows spring (316) to collapse and pull the edges of infarct (302) incrementally towards each other. FIG. 3A shows, as mentioned above, the placement of inventive device (306) shortly after introduction to the heart surface.

FIG. 3B shows the placement of the inventive device (306) after ingrowth of myocardial tissue into the heart tissue adherence regions (308) or other fixation of the adherence regions (308) onto the heart tissue.

Finally, FIG. 3C shows the approach of the myocardium regions and the eventual collapse of the spring to its lowest energy configuration. A region of reformed tissue (318) may be produced depending upon a wealth of variables such as the health of the patient and the heart, the speed with which the springs (316) moved the affected tissue, the size of the infarct, etc. This region of reformed tissue (318) has been created by the disappearance of the time delay member (318) (shown in FIGS. 3A and 3B) from the center of spring (316). Spring (316) then pulls together the two opposing portions of the inventive device (306) and maintains an appropriate support to the tissue between the two opposing tissue regions (304).

A substantial but desirable variation of the invention is to form the springs (316) from a material, typically polymeric, having both sufficient biodegradability and springiness to act as the time-delay component discussed above and as the component that provides movement between the opposing adherence regions of the inventive device, such as may be provided by the springs (316) above. This variation allows a major component of the device to be absorbed into the body after the end of its functional life. Oriented polyglycolide and polylactide-based polymers (and other polymeric materials listed below) that have been sized and formed into spring structures are particularly suitable for this variation.

In any case, the associated covering or composition preferably is a polymeric material such as a biodegradable polymer, e.g., polyglycolic acid, polylactic acid, reconstituted collagen, poly-p-dioxanone, and their copolymers such as poly(glycolide-lactide) copolymer, poly(glycolide-trimethylene carbonate) copolymer, poly(glycolide-ε-caprolactone) copolymer, glycolide-trimethylene carbonate triblock copolymer, and the like. Mixtures of the noted polymers, e.g., of polylactide and polyglycolide may also be used.

The various time-delay components discussed here may be produced using materials that are biocompatible and preferably either metallic or polymeric. Acceptable polymeric compositions are discussed just above. Appropriate materials for these inventive devices include alloys such as super-elastic alloys. Super-elastic or pseudoelastic shape-recovery alloys are well known in this art. For instance, U.S. Pat. Nos. 3,174,851; 3,351,463; and 3,753,700 each describe one of the more well known super-elastic alloys, known as Nitinol. These alloys are characterized by their ability to be transformed from an austenitic crystal structure to a stress-induced martensitic (SIM) structure at certain temperatures and then to return elastically to the austenitic shape when the stress is removed. These alternating crystal structures provide the alloy with its super-elastic properties. The alloy mentioned in the three patents just above, is a nickel-titanium alloy. It is readily commercially available and undergoes the austenitic-SIM-austenitic transformation at a variety of temperatures between –20° C. and +30° C.

These alloys are especially suitable because of their capacity to recover elastically, almost completely, to the initial configuration once the stress is removed. Typically, in services such as are described here, there is little permanent plastic deformation even at relatively high strains. This ability allows the time-delay component to retainer device to undergo substantial bending both during delivery through various minimally invasive devices and to return to its least-stressed form and contract the nearby infarct as any time-delay polymeric covering reacts, dissolves, or is absorbed.

The transition temperature of this material is not particularly important, but it should be reasonably below the typical temperature of the human body so to allow it to be in its austenitic phase during use. The diameter of the wires or ribbons making up the various time-delay element but are typically smaller than about 0.010 inches in diameter. However, they need only be sized appropriately for the production and maintenance of the infarct support as specified elsewhere.

Super-elastic alloys are not always suitably visible under fluoroscopy as it is used on the human body. Consequently it may be desirable to add a covering of some kind to improve the radio-opacity of the component. Radio-opaque metals such as gold and platinum are well known. They may be added the various elements of this inventive device by such widely recognized methods as by plating or by wrapping the element in a radio-opaque wire or ribbon.

Specific members of other classes of suitable super-elastic alloys include: Monel alloys such as MP35N, SYNTACOBEN, and cobalt/chromium alloys such as ELGILOY, etc.

Although we have discussed producing the spring member from super-elastic alloys, other metals may in certain circumstances be appropriate. Such metals include a number of the stainless steels (for instance, SS308, SS304, SS318, etc.) and other highly elastic, if not super-elastic, alloys. The support-inducing member may further be produced from other metals or alloys known as suitable springs, e.g., tantalum, tungsten, titanium, silver, gold, platinum, and alloys of these materials.

Figure 4A:
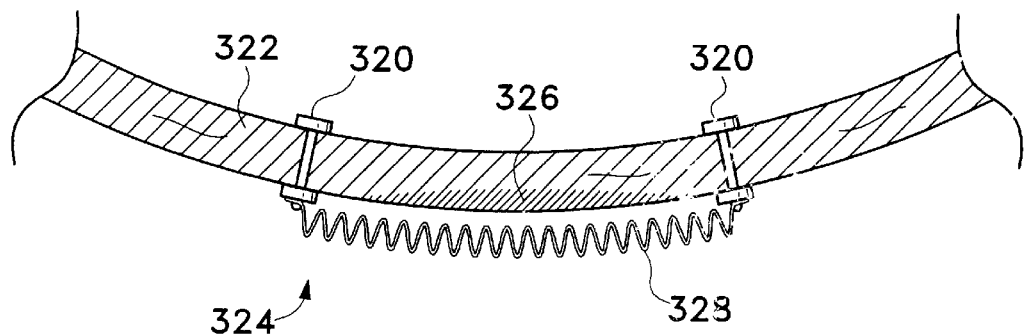
FIGS. 4A, 4B, and 4C are similar to FIGS. 3A–3C but depict a differing use of the time delay element of the inventive device.
Figure 4B:
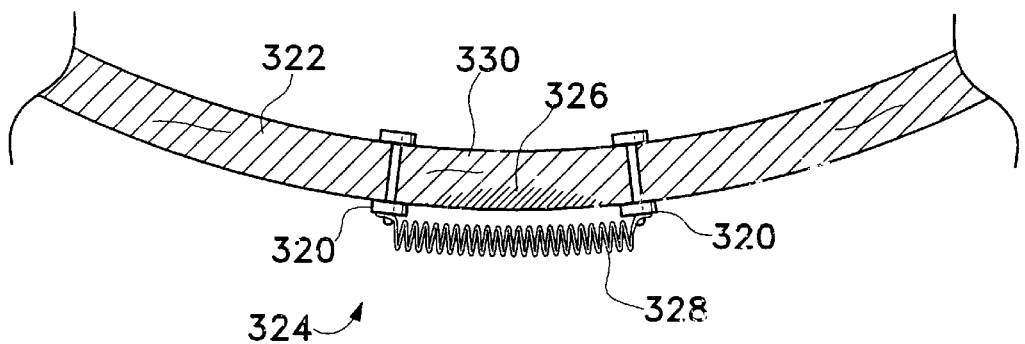
Figure 4C:
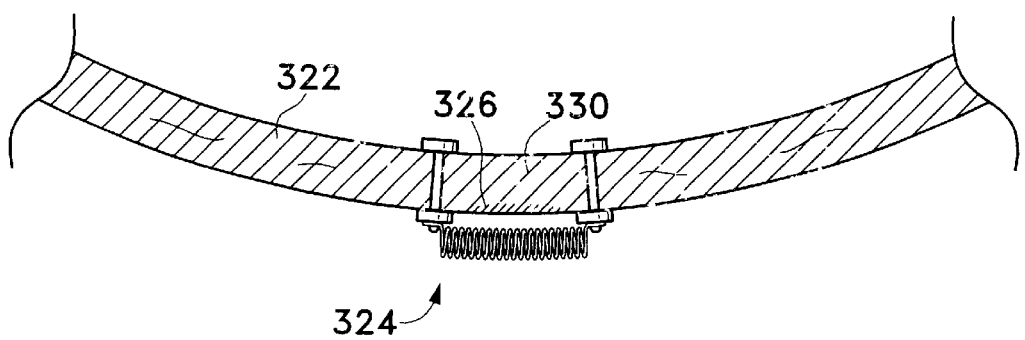

FIGS. 4A, 4B, and 4C show, in concept, the proposed operation of the device such as depicted in FIG. 2B.

In this variation, the device employs mechanical fasteners (320) that penetrate the ventricular wall (322) to hold the inventive device (324) in place about infarct (326). The spring (328) in this variation is coated with a biodegradable or bioerodable covering or, as an alternative, comprises a biodegradable polymer. In the latter case, as the bioerodable covering thins, spring (128) decreases in length between the two depicted fasteners (320) and provides support to the tissue between those fasteners (320).

FIG. 4B shows the infarct (326) site at a later time. The regions of comparatively healthier myocardial tissue (330) have thickened and the distance between two fasteners (32) has decreased as the covering on spring (328) has eroded.

FIG. 4C shows a still further stage in recovery of the ventricular wall (322) and the specific region (330) interior to infarct (326).

As noted elsewhere, the inventive device desirably includes at least three components: at least a first heart tissue adherence region, at least one second heart tissue adherence region that is either separable or separated from the first tissue adherence region, and at least one tissue supporting member situated (with respect to the first and second heard tissue adherence regions) so to maintain support to the tissue (usually containing an infarcted area) between the first and second tissue adherence regions when the device has been introduced onto the heart surface. Highly preferable is a variation of the tissue supporting member that involves a "time delay" feature. This feature permits a change of the spring length between the first and second heart tissue adherence regions with time.

It is desirable that the inventive device be adapted to promote angiogenesis in the myocardial wall both adjacent the various tissue contact regions and throughout the pericardial space. Angiogenesis-promoting materials, particularly those that promote growth of microvasculature, whether synthetic or natural may be infused into the various components of the inventive device or introduced into the pericardial space during placement of the device. Introduction of angiogenesis-promoting materials into the supporting region, into or onto the polymers acting as time-delay coatings or springs, and generally placed adjacent the infarct regions and their peripheries is seen to be a desirable enhancement of the healing process. Angiogenic materials include, e.g., collagen, fibrinogen, vitronectin, other plasma proteins, various appropriate growth factors (e.g., vascular endothelial growth factor, "VEGF"), and synthetic peptides of these and other similar proteins. Other components having a specific role may be included, e.g., genes, growth factors, biomolecules, peptides, oligonucleotides, members of the integrin family, RGD-containing sequences, oligopeptides, e.g., fibronectin, laminin, bitronectin, hyaluronic acid, silk-elastin, elastin, fibrinogen, and the like.

Other bioactive materials which may be used in the invention include, for example, pharmaceutically active compounds, proteins, oligonucleotides, ribozymes, and antisense genes. Desirable additions include vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directly against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms, and combinations thereof.

In addition, polypeptides or proteins that may be incorporated into or onto the inventive device, or whose DNA can be incorporated, include without limitation, proteins competent to induce angiogenesis, including factors such as, without limitation, acidic and basic fibroblast growth factors, vascular endothelial growth factor (including VEGF-2, VEGF-3, VEGF-A, VEGF-B, VEGF-C) hif-1 and other molecules competent to induce an upstream or downstream effect of an angiogenic factor; epidermal growth factor, transforming growth factor α and β, platelet-derived endothelial growth factor, platelet-derived growth factor, tumor necrosis factor α, hepatocyte growth factor and insulin like growth factor; cell cycle inhibitors including CDK inhibitors; thymidine kinase ("TK") and other agents useful for interfering with cell proliferation, and combinations thereof.

By the term "adherence," we mean that the noted heart tissue adherence region of the inventive device is substantially immobile with respect to its related heart tissue. That is to say that a tissue adherence region may be adhesively connected to the tissue, mechanically attached to the tissue, ingrown with the tissue, connected using specific mechanical connectors, or other methods of or means for preventing relative motion between the device component and the tissue wall.

We consider it generally undesirable to incur adhesion of the device to the myocardium and to the pericardium except in the areas specifically selected for adhesion. A variety of methods are appropriate for preventing such adhesion. However, one highly effective way is to select materials of construction that do not usually adhere to heart tissue. Such materials include polymers such as polyfluorocarbons and polyolefins particularly those selected from the group consisting of polytetrafluoroethylene (PTFE or TFE), ethylene-chlorofluoroethylene (ECTFE), fluorinated ethylene propylene (FEP), polychlorotrifluoroethylene (PCTFE), polyvinylfluoride (PVF), polyvinylidenefluoride (PVDF), polyethylene (LDPE, LLDPE, and HDPE), and polypropylene.

Figure 5:
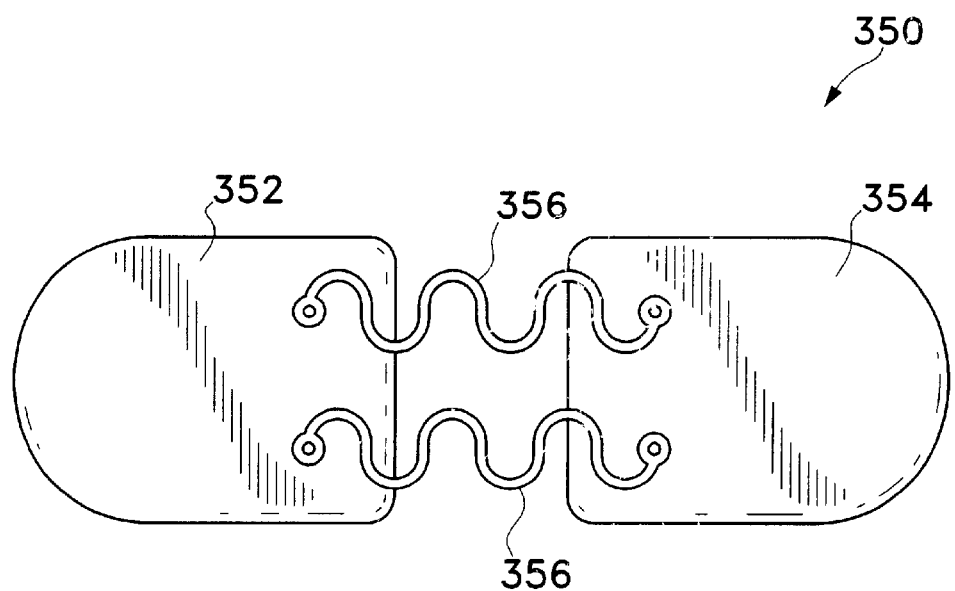
FIGS. 5 and 6 show variations of the inventive device.

FIG. 5 shows a variation (350) of the inventive device having a first tissue contact pad (352) which, of course, makes up the first heart tissue adherence region, and a second tissue contact pad (354), typically of a similar composition and size to the first contact pad (352). The two pads are shown in FIG. 5 to be separated and to be separable.

Also shown in FIG. 5 are two spring support maintaining members (356). In this instance, they comprise springs (356) that are fixedly attached to each of the tissue contact pads (352, 354). Each of tissue contact pads (352, 354) may be made to adhere to the heart by any of the methodologies discussed above and discussed in more detail below. For instance, the pads may be glued to the myocardial surface suing appropriate adhesives such as fibrin-based glues or cyanoacrylates. Other suitable biological adhesives would obviously also be useful on these devices. As is the case with each of the tissue contact pads listed in the variations discussed below, the pads may be held in a position to allow to intergrow with heart tissue if suitable treatment permits long-term placement of the device in alleviating the injury. The contact pads may be mechanically fastened to the heart muscle by mechanical fasteners as discussed elsewhere.

The nature of the support-inducing members, shown as springs (356), is not critical in that the member or members may be polymeric or rubbery materials but preferably are springs as shown in the figure. The springs (356) shown in FIG. 5 are flat springs to minimize the overall thickness of the device and the U-shaped turns of the springs provide a substantially linear spring rate upon spring compression. As discussed elsewhere, the depicted springs (356) may include coatings to permit change of spring length over time.

Figure 6:
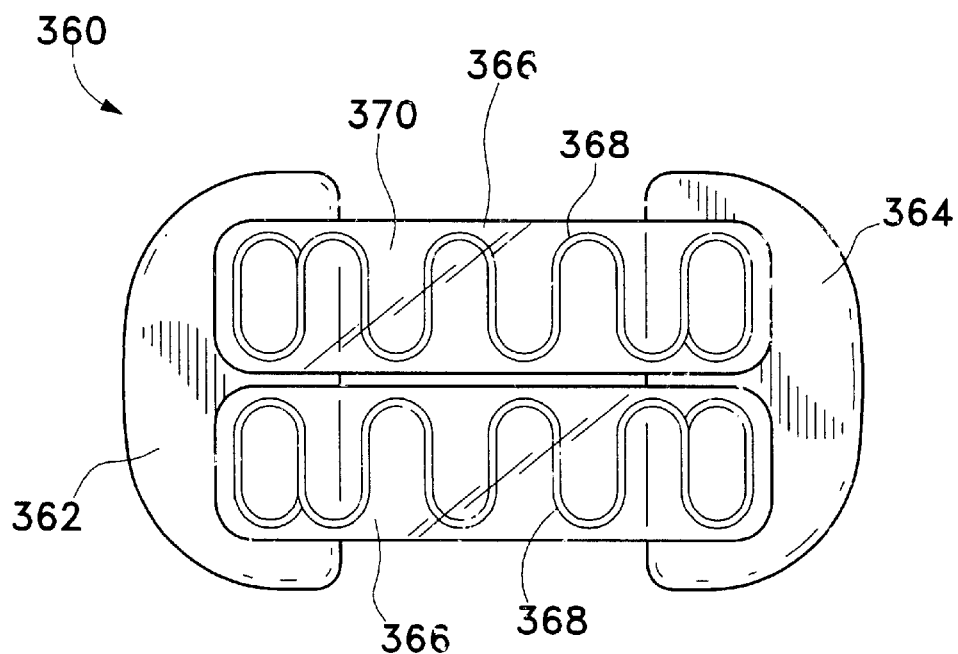

FIG. 6 shows a variation of the inventive device (360) similar in overall function and view to that found in FIG. 5. It includes a first tissue contact region (362) and a second tissue contact region (364) separated from the first. The support inducement and maintenance components (366) in this variation are shown to be embedded springs (368) having a biodegradable or bioerodable overall covering (370), as also discussed elsewhere. These support inducing members are intended to provide a constant stiffness between the two tissue contact surfaces (362, 364). This means that the springs are somewhat stretched during placement into the covering material (370). As the covering (370) erodes, the embedded springs (368) are allowed to relax and the spring length becomes shorter, thereby all the while providing a specific rigidity to the infarcted tissue region between the ends of the inventive device.

Figure 7A:
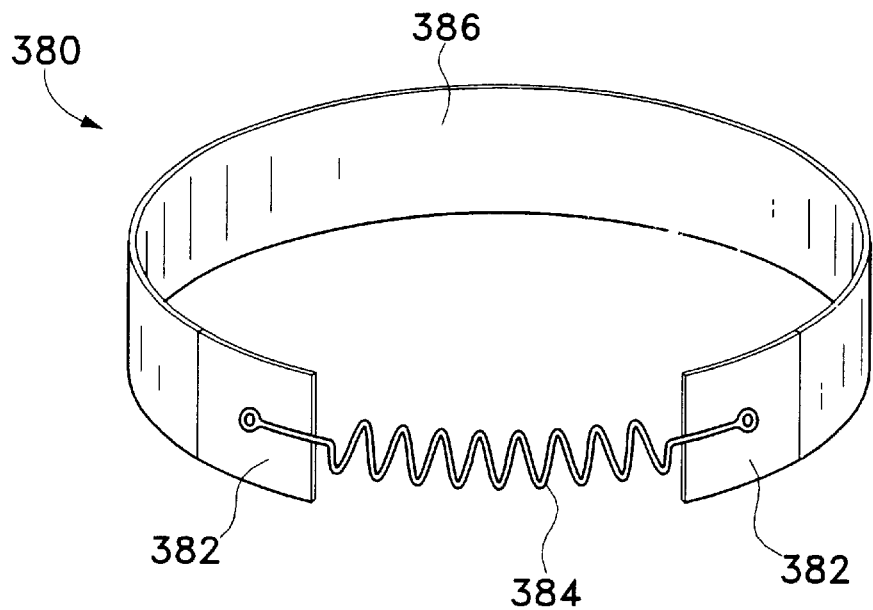
FIG. 7A shows a variation of the device including a band to be wrapped around a diseased heart.

FIG. 7A shows a variation (380) of the inventive device having dual heart tissue contact regions at (382) and a support inducing member (384), here depicted as a coil spring. In addition, this variation includes a band (386) which extends from one tissue contact region (382) to the other tissue contact region (382). The band (386) is used to surround the heart and to position the various active components of inventive device (380) properly about the infarct region. The band (386) is typically made of a material which tends not to allow intergrowth or adhesion to heart tissue.

Figure 7B:
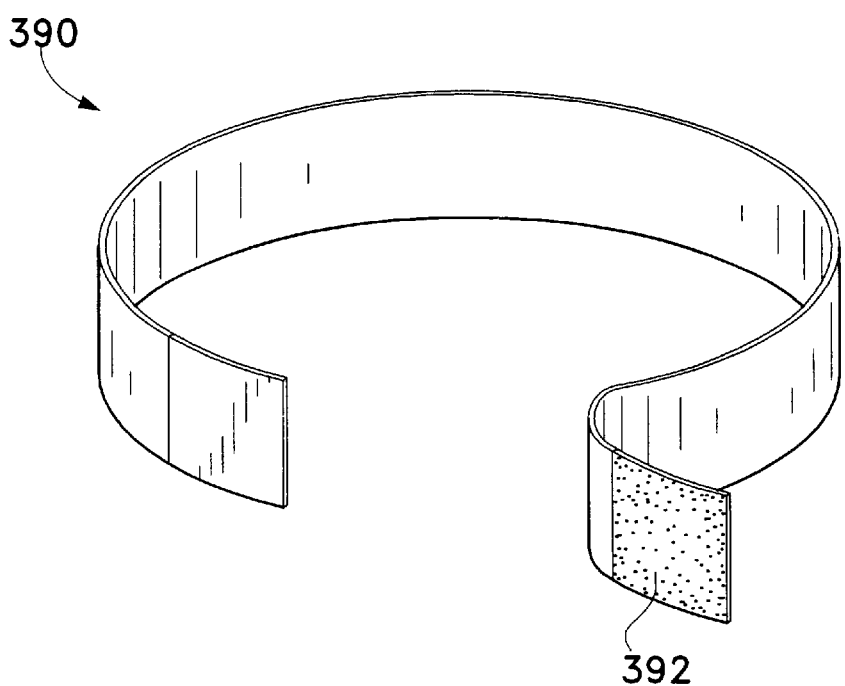
FIG. 7B shows the device shown in FIG. 7A without the support inducing element.

FIG. 7B shows the device (380) without the spring (384). This portion of the device shows an inner contact region (392) which may be adapted to aid with biologic or chemical adhesion of device (390) to heart tissue.

FIGS. 8A and 8B show side view and cross-sectional views of one variation of springs (400) useful as a support inducing member and as a time delay element. In this variation, the spring (402) of a bioerodable or biodegradable material. Suitable coverings include polymeric materials such as a biodegradable polymer, e.g., polyglycolic acid, polylactic acid, reconstituted collagen, poly-p-dioxanone, and their copolymers such as poly(glycolide-lactide) copolymer, poly(glycolide-trimethylene carbonate) copolymer, poly(glycolide-ε-caprolactone) copolymer, glycolide-trimethylene carbonate triblock copolymer, and the like. Copolymers, mixtures, and alloys of the noted polymers, e.g., of polylactide and polyglycolide may also be used. The turns in this spring are flat and approximately "U"-shaped.

FIG. 9A shows a side view of a combination support inducing member and time delay member (406) made up of a spring (408) and its attendant bioerodable or biodegradable covering (410). In this variation, the covering is cast generally as a slab with the spring inside. In this variation, the spring (408) is flat and has loops at the end of the coil undulations. Again, this spring form provides a reasonably linear rate/spring length relationship.

FIGS. 10A and 10B show a coil spring (416) which an interior time delay element (418). The time delay element (418) in this variation is a composite component having an inner stripe of biodegradable or bioerodable polymer (420) and an outer partial covering of nonerodable material (422). The partial outer covering (422) may be considered a U-shaped component having an erodable polymer inside the arms of the U. This variation allows degradation or erosion of the inner polymer along the exposed edge and the inner stiffener (418) will bend with time allowing the spring to collapse and pull and shorten.

Figure 11:
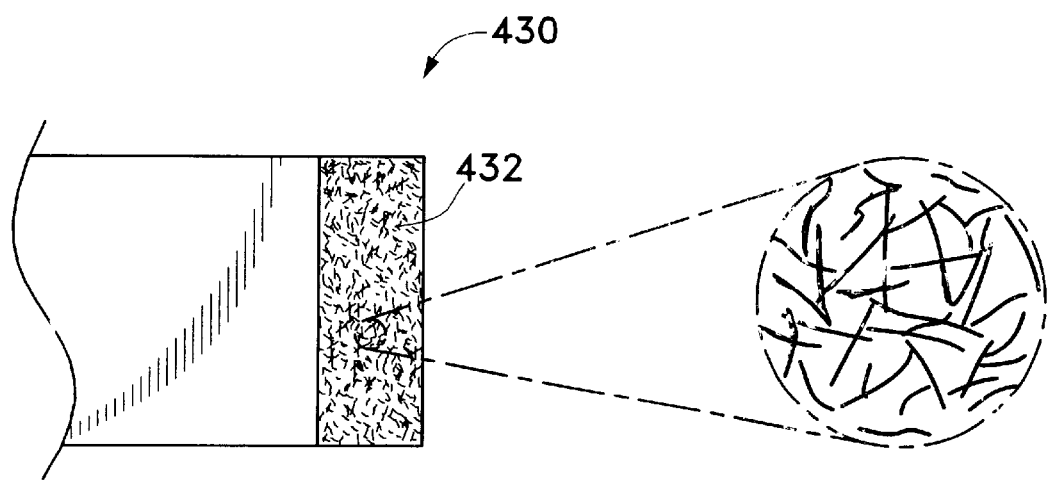
FIGS. 11 and 12 show a number of surfaces for the tissue adherence regions of the inventive device.

FIG. 11 shows the inner surface of a variation of the inventive device (430). Surface (432) is the heart tissue contact surface. This surface (432) is roughened and will allow creation of a biological bond with the heart muscle it contacts given the appropriate amount of time.

Figure 12:
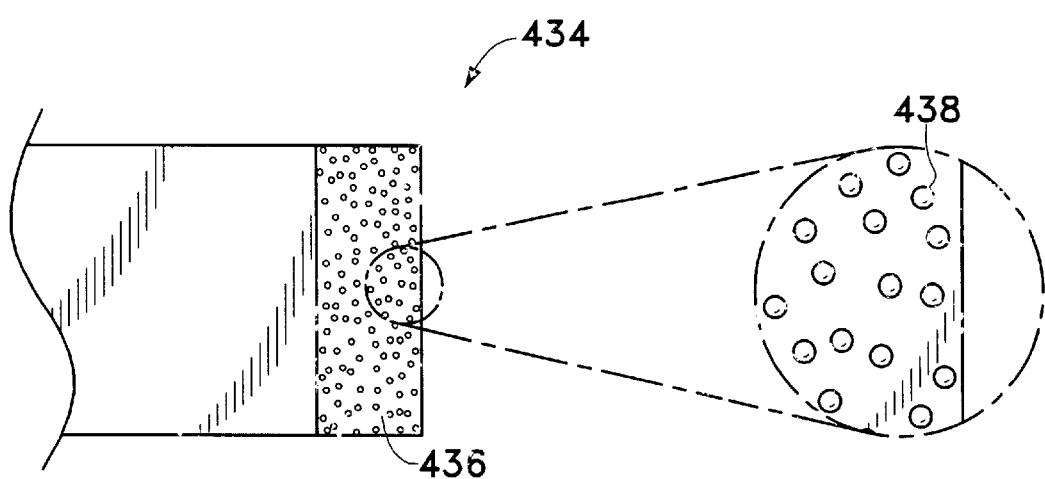

Similarly, FIG. 12 shows a device 434 having a surface (436) having small "nubs" (438) which are small hillocks which tend to promote mechanical attachment to heart muscle. In the variation shown in FIGS. 11 and 12, it is highly desirable that the contact areas (432) in FIG. 11 and (436) in FIG. 12 be surrounded by (or at least partially surrounded by) material which tends not to adhere to or create biological adherence to the heart muscle.

FIGS. 13A to 13D show a procedure for introducing a mechanical tissue fastener (450) through the inventive device (452) and the myocardial wall (454).

Figure 13A:
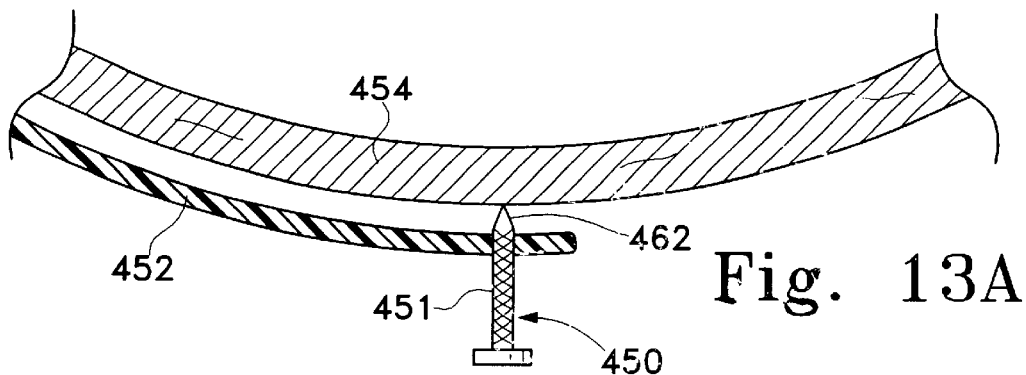
FIGS. 13A to 13D show a procedure for introducing a mechanical fastener onto a myocardial wall to cause the inventive device to adhere to that wall.
Figure 13B:
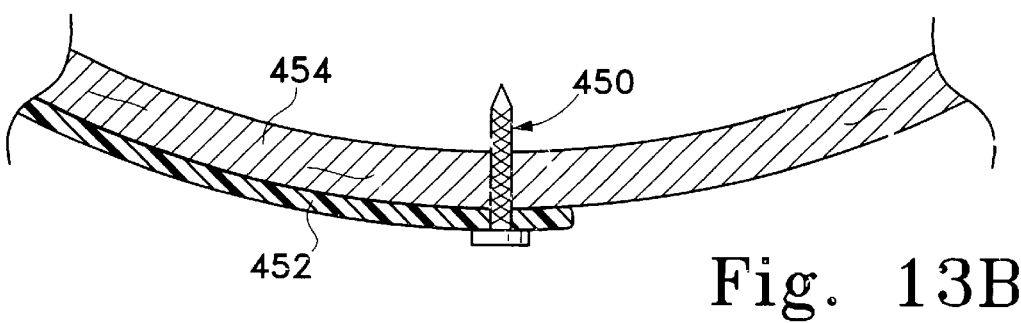

As shown in FIG. 13A, the fastener (450) and contact region (452) are positioned appropriately at the site chosen on myocardium (454). In FIG. 13B, the mechanical fastener (450) having a penetrating shaft (451) ending in a piercing end (462) has penetrated the myocardial wall (454) and the contact region (452) has been snugged down against the myocardial wall (454).

Figure 13C:
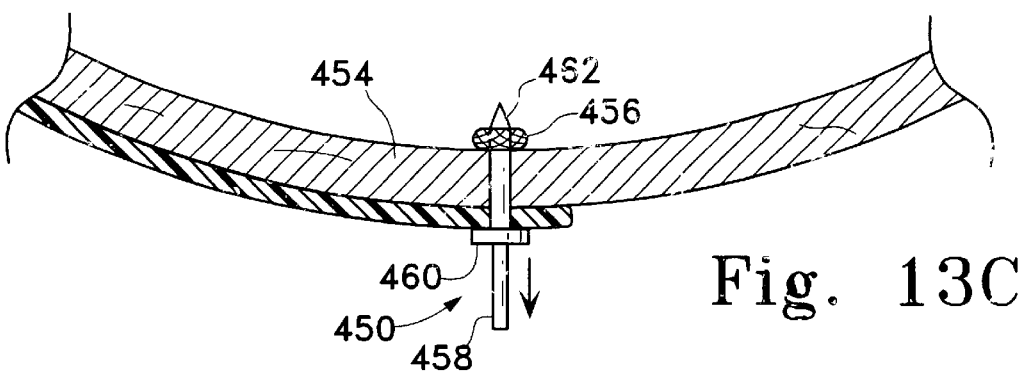

FIG. 13C shows the spreading of braid (456) interior to myocardial wall (454). This mechanical adhering device (450) has an inner shaft (458), a collar (460), and a piercing end (462). The inner shaft (458) may be moved against the collar (460) to expand braid (456) to allow the device to be held against the inner heart wall.

Figure 13D:
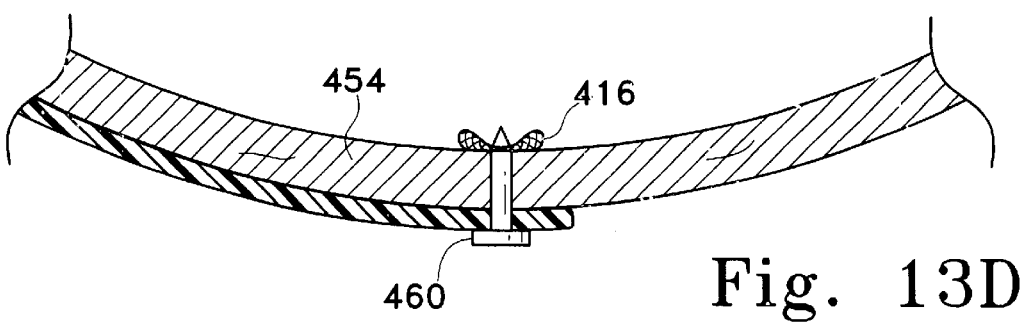

FIG. 13D shows the final step in which the braid (456) is flattened against the inner wall of the myocardium (454). The inner shaft (458) has been removed and collar (460), in conjunction with braid (456), holds the device in position for use.

This inventive device is quite tidy and because it generally has but a localized placement on the heart, is suitable for placement on the myocardium via any number of procedures, ranging from the most invasive—open chest surgery—to those that are much less invasive. A preferred procedure for placing the device is via a percutaneous approach through the diaphragm beneath the xiphoid process. It is direct and uses short instruments for ease and accuracy. Such a process is outlined in FIGS. 14A–14F.

Figure 14A:
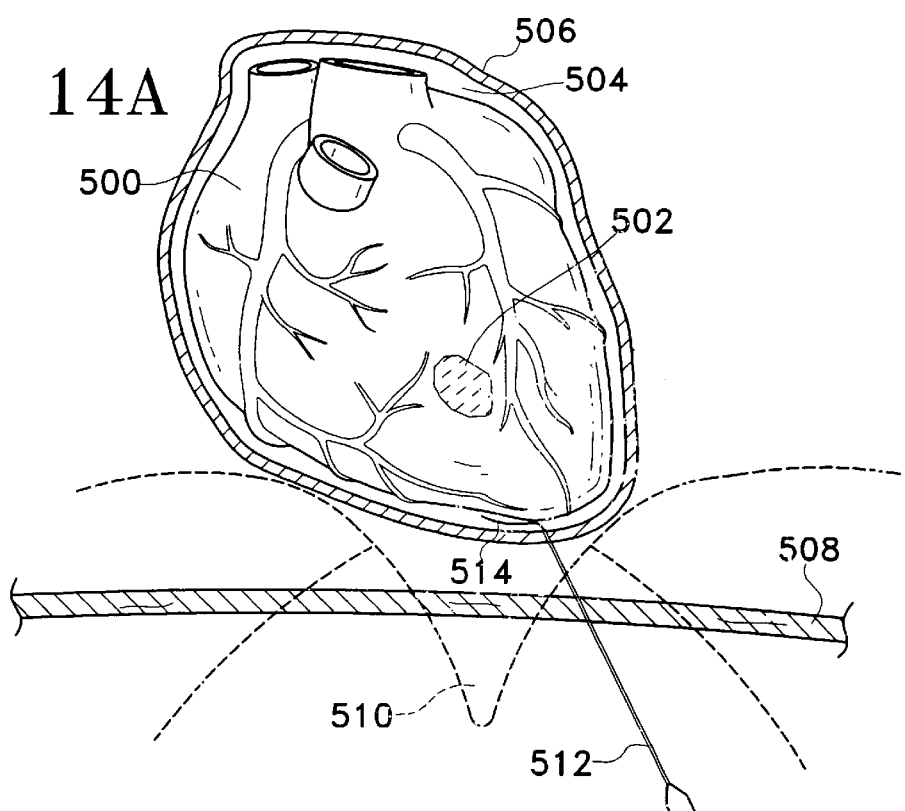
FIGS. 14A to 14F show a procedure for introducing the inventive device to the heart via a subxiphoid approach.

Shown in FIG. 14A is a heart (500) having an infarct (502) in the right ventricular wall. The heart (500) is surrounded by a pericardial space (504) holding pericardial fluid and all is enclosed by the pericardium (506). Also shown is the muscle sheet known as the diaphragm (508). For the purposes of depicting the spatial relationships in this procedure, also shown (in shadow) is the xiphoid process (510) and some nearby rib and sternal structure. Much of the extraneous body structure not otherwise needed for explanation of the procedure has been omitted for clarity.

Also shown in FIG. 14A is the first step of the procedure. A suitably large hollow needle (512) and a guidewire (514) passing through the lumen of the needle (512) have been introduced below the xiphoid process (510) and through the diaphragm (508). The needle (512) and the guidewire (514) are shown having penetrated the pericardium (506).

Figure 14B:
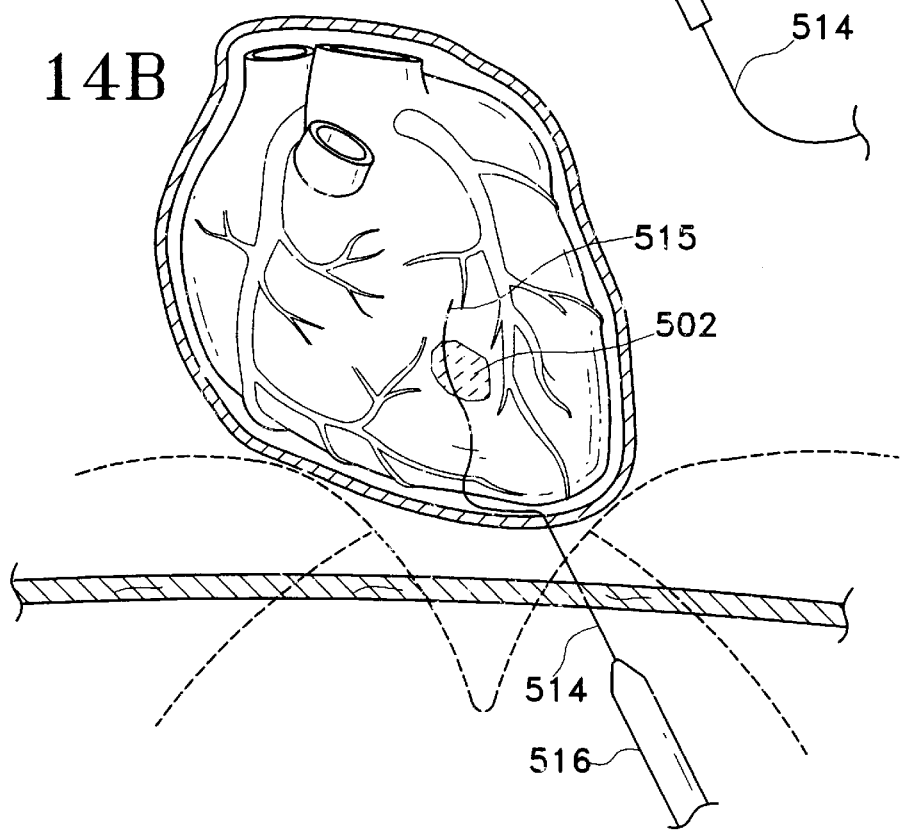

FIG. 14B shows that the needle has been removed from the guidewire (514) and the distal end (515) of the guidewire (514) has been manipulated to pass by the infarcted region (502). An introducer or cannula (516) is shown being passed up the guidewire (514).

Figure 14C:
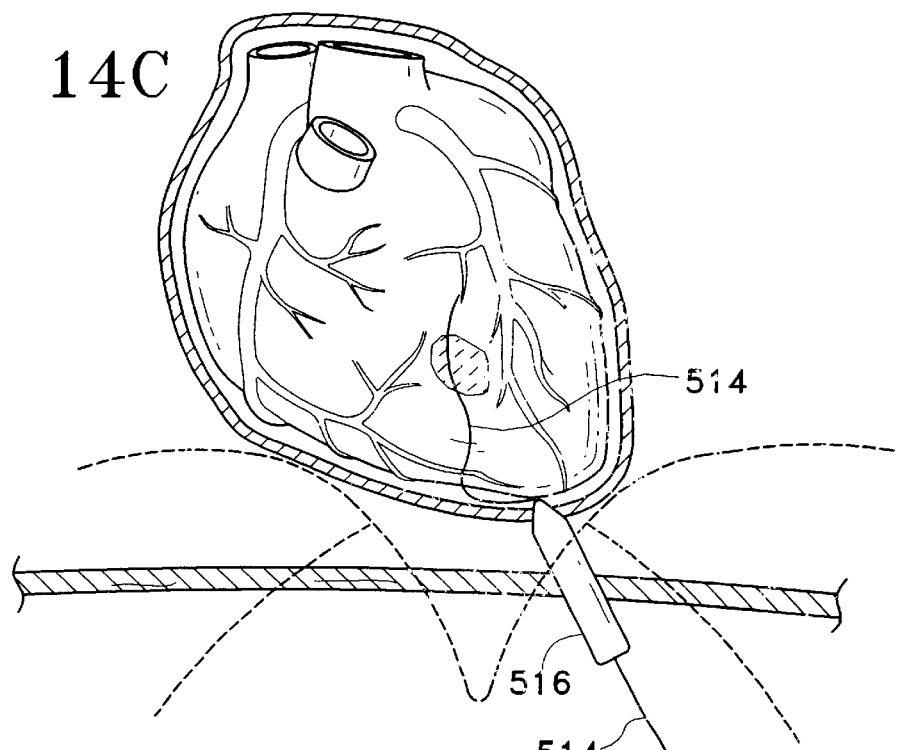

FIG. 14C shows placement of the introducer or cannula (516). The tip of delivery catheter (518) is shown passing up the guidewire (514) and towards the lumen of introducer or cannula (516).

Figure 14D:
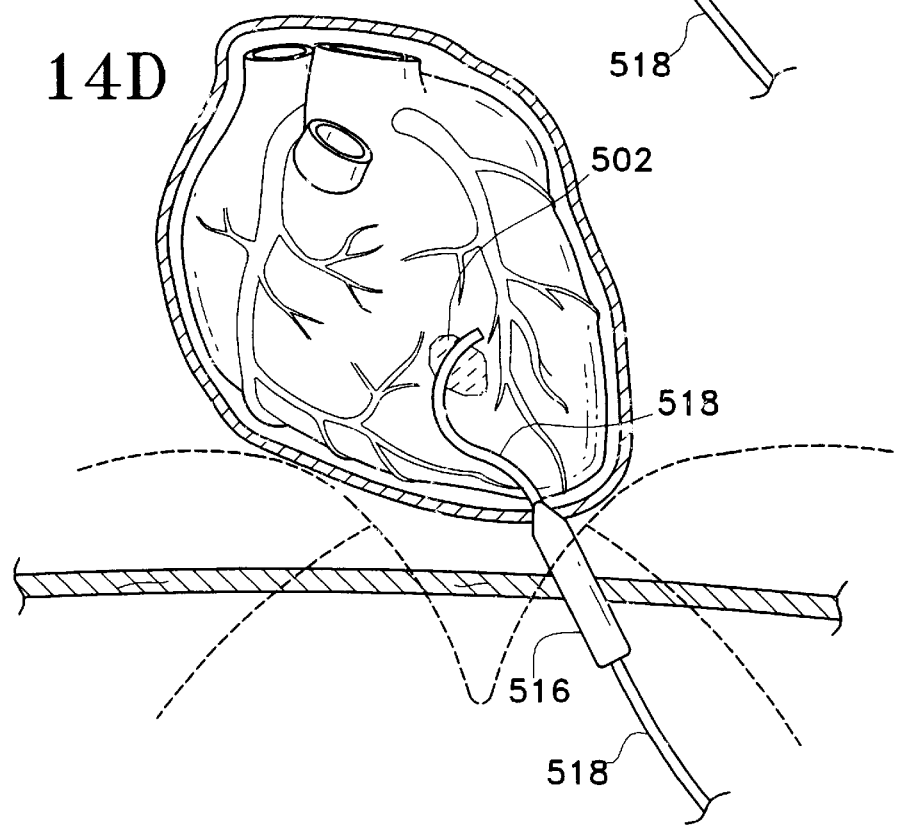

FIG. 14D shows placement of the delivery catheter (518) through the introducer or cannula (516) and up onto the region of the heart having the infarct (502). The guidewire (514) has been removed.

Figure 14E:
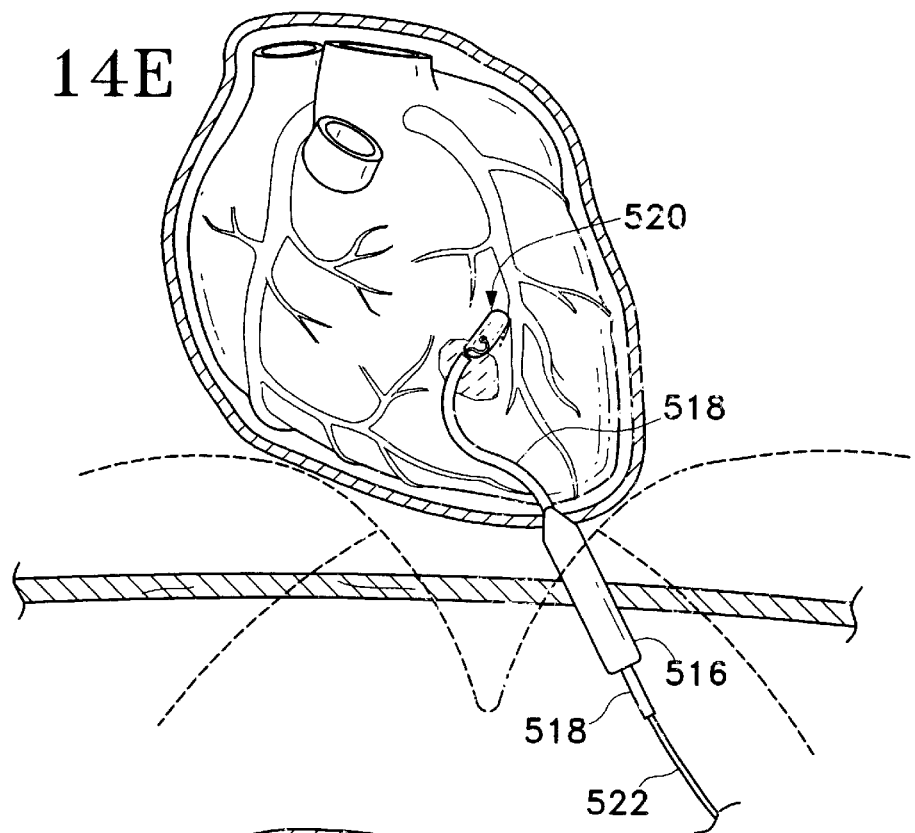

FIG. 14E depicts the step of deploying the inventive device (520) across the infarct (502). In this variation, the inventive device (520) is introduced into the lumen of the delivery catheter (518) and pushed through the catheter (518) by use of a pusher (522).

Figure 14F:
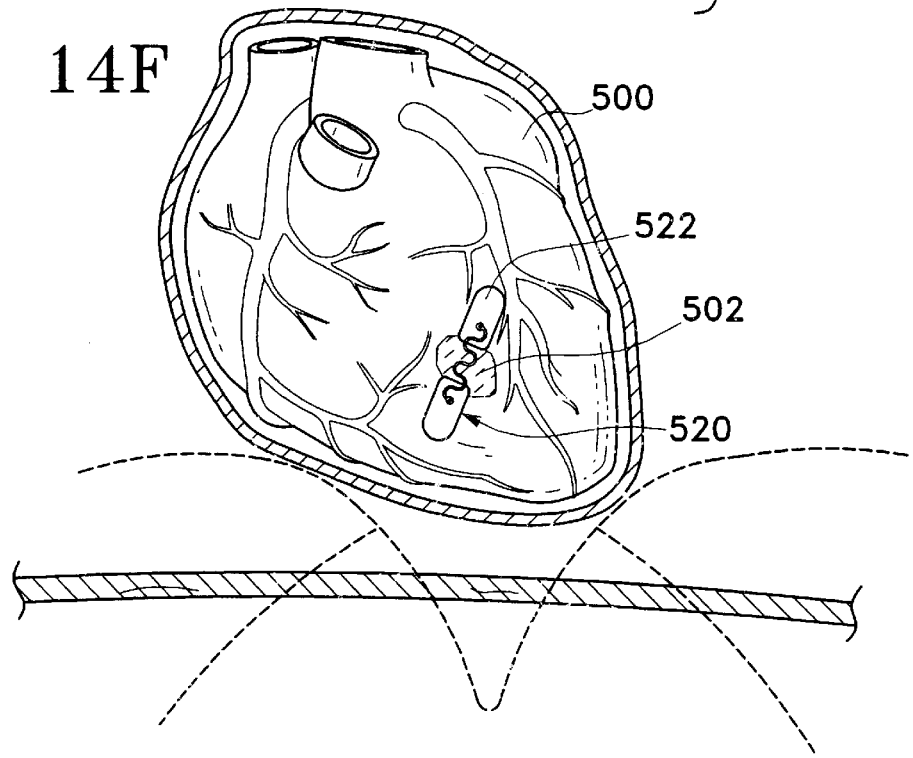

FIG. 14F shows the final positioning of the inventive device (520) over the infarct (502) on the heart (500). The support inducing and maintenance member (522) may be seen extending over the opposing sides of the periphery of the infarct (502).

Not discussed with relation to FIGS. 14A–14F is a step of affixing the inventive device (522) to the heart (500). However, the procedures discussed with relation to FIGS. 13A–13D may be applied independently, for instance, to so cause adherence between the device and the heart. Separate tubing members for introduction of adhesives to the appropriate regions of the heart or device are also suitable.

Many alterations and modifications may be made by those of ordinary skill in this art, without departing from the spirit and scope of this invention. The illustrated embodiments have been shown only for purposes of clarity and the examples should not be taken as limiting the invention as defined in the following claims. Which claims are intended to include all equivalents, whether now or later devised.

What is claimed is:

1. A heart tissue supporting device comprising:
 a.) at least one first heart tissue adherence region and each adapted to adhere to selected first heart tissue regions on a heart surface, b.) at least one second heart tissue adherence region separated from the at least one first heart tissue adherence regions and each adapted to adhere to selected second heart tissue regions on a heart surface, and c.) at least one support-providing member comprising at least one coil spring having opposing ends attached between the at least one first heart tissue adherence region and the at least one second heart tissue adherence region, said member being situated to maintain support to tissue between the at least one first heart tissue adherence region and the at least one second heart tissue adherence region, wherein each heart tissue adherence region is further adapted to be approximated towards one another along the heart surface.

2. The heart tissue supporting device of claim 1 where at least one of first heart tissue adherence regions and second heart tissue adherence regions is at least partially surrounded by a region that is substantially non adhering to heart tissue.

3. The heart tissue supporting device of claim 2 where the material forming at least a portion of the non adhering regions at least partially surrounding the at least one first heart tissue adherence region and the at least one second heart tissue adherence region is selected form the group consisting of woven or non-woven polymeric fabrics selected from the group consisting of polyfluorocarbons and polyolefins.

4. The heart tissue supporting device of claim 3 where the polyflurocarbons and polyolefins are selected from the group consisting of polytetrafluoroethylene (PTFE), ethylene chlorofluoroethylene (ECTFE), fluorinated ethylene propylene (FEP), polychlorotrifluoroethylene (PCTFE), polyvinylfluoride (PVF), polyvinylidenefluoride (PVDF), polyethylene (LDPE, LLDPE and HDPE), and polypropylene.

5. The heart tissue supporting device of claim 1 where the at least one support providing member is sized and placeable to maintain a first heart tissue contact region positioned against a second heart tissue contact region.

6. The heart tissue supporting device of claim 1 further including a connector strap that is substantially non adhering to heart tissue and is configured to connect the at least one first heart tissue adherence region and the at least one second heart tissue adherence region and thereby form, with the at least one support providing member, a loop adapted to surround a heart having the first and second heart tissue regions.

7. The heart tissue supporting device claim 6 where the material forming at least a portion of the connector strap is selected from the group consisting of woven or non-woven polymeric fabrics selected from the group consisting of polyfluorocarbons and polyolefins.

8. The heart tissue supporting device of claim 7 where the polyfluorocarbons and polyolefins are selected from the group consisting of polytetrafluoroethylene (PTFE or TFE), ethylene chlorofluoroethylene (ECTFE), fluorinated ethylene propylene (FEP), polychlorotrifluoroethylene (PCTFE), polyvinylfluoride (PVF), polyvinylidenefluoride (PVDF), polyethylene (LDPE, LLDPE, and HDPE), and polypropylene.

9. The heart tissue supporting device of claim 1 where at least one of the first heart tissue adherence regions and the second heart tissue adherence regions comprises an adhering material selected to allow ingrowth of heart tissue into those regions.

10. The heart tissue supporting device of claim 9 where the adhering material is selected form the group consisting of woven or non-woven polymeric fabrics.

11. The heart tissue supporting device of claim 10 where the woven or non-woven polymeric fabrics selected from polyethyleneterephthalate, cotton, and expanded polyfluorocarbons having internodal spacing suitable for intergrowth.

12. The heart tissue supporting device of claim 11 where the support providing member further comprises a time delay member adapted to provide a period of time over which the distance between the at least one first heart tissue adherence region and the at least one second heart tissue adherence region varies.

13. The heart tissue supporting device of claim 12 where the time-delay member comprises a biodegradable material.

14. The heart tissue supporting device of claim 12 where the time-delay member is coated with a biodegradable material.

15. The heart tissue supporting device of claim 12 where the time-delay member is embedded in a biodegradable material.

16. The heart tissue supporting device of claim 12 where the time-delay member comprises a biodegradable material.

17. The heart tissue supporting device of claim 12 where the support providing member comprises a spring and the time-delay member comprises a biodegradable material member tending to hold the spring in extension until after functional biodegradation in the human body.

18. The heart tissue supporting device of claim 12 the time delay member is treated with at least one angiogenesis composition.

19. The heart tissue supporting device of claim 12 the time-delay member comprises at least one angiogenesis composition.

20. The heart tissue supporting device of claim 1 where the support providing member further comprises a time delay member adapted to provide a period of time between an introduction of the heart tissue supporting member into a human body and initiation of a movement of the at least one first heart tissue adherence region towards the at least one second heart tissue adherence region.

21. The heart tissue supporting device of claim 2 where the time-delay member comprises a biodegradable material.

22. The heart tissue supporting device of claim 1 where at least of the one first heart tissue adherence region and the at least one second heart tissue adherence regions includes a surface selected to allow ingrowth of heart tissue into those regions.

23. The heart tissue supporting device of claim 22 where the surface is not smooth.

24. The heart tissue supporting device of claim 22 where the surface is roughened.

25. The heart tissue supporting device of claim 22 where the surface is nubbed.

26. The heart tissue supporting device of claim 22 where the surface is perforated.

27. The heart tissue supporting device of claim 22 where the surface is treated with at least one angiogenesis composition.

28. The heart tissue supporting device of claim 1 where at least a portion of the heart tissue supporting member is treated with at least one angiogenesis composition.

29. The heart tissue supporting device of claim 1 where at least one of the first heart tissue adherence region and second heart tissue adherence region support providing member are treated with at least one angiogenesis composition.

30. The heart tissue supporting device of claim 1 where at least of the one first heart tissue adherence region and the at least one second heart tissue adherence regions includes a mechanical fastener adapted to perforate heart tissue and cause adherence to those regions.

31. The heart tissue supporting device of claim 1 where at least of the one first heart tissue adherence region and the at least one second heart tissue adherence regions includes a surface including an adhesive selected to cause heart tissue adhesion onto those regions.

32. A method for providing support to a myocardial wall across an infarct, comprising the steps of
  a.) adhering a first tissue contact area of a supporting member to the myocardial wall at a first tissue site adjacent the infarct,
  b.) adhering a second tissue contact area of the supporting member to the myocardial wall at a second tissue site adjacent the infarct but adapted for positioning the supporting member across the infarct, and
  c.) advancing the first tissue contact area towards the second tissue contact area along a surface of the myocardial wall, wherein the step of advancing the first tissue contact area towards the second tissue contact area comprises eroding a bioerodible material situated between the first and second tissue contact areas.

33. The method of claim 32 where the steps of adhering the first and second tissue contact areas respectively to first and second tissue sites comprises placing adhesive respectively between the first and second tissue contact areas and the first and second tissue sites.

34. The method of claim 32 where the steps of adhering the first and second tissue contact areas respectively to first and second tissue sites comprises mechanically attaching the first and second tissue contact areas respectively to the first and second tissue sites.

35. The method of claim 32 where the bioerodible material is associated with a support providing member in such a way to tend to hold spring attached to the first and second tissue contact areas in extension until the material has degraded.

36. The method of claim 32 where the bioerodible material comprises a support-providing member.

37. A method for supporting a localized or regional area of a heart comprising the steps of
  a.) adhering a first tissue contact area of a supporting member to the heart at a first tissue site adjacent a region to be supported,
  b.) adhering a second tissue contact area of the supporting member to the heart at a second tissue site adjacent the region to be supported but adapted for positioning the supporting member across the region to be supported, and
  c.) advancing the first tissue contact area towards the second tissue contact area along a surface of the heart, wherein the step of advancing the first tissue contact area towards the second tissue contact area comprises eroding a bioerodible material situated between the first and second tissue contact areas.

38. The method of claim 37 where the steps of adhering the first and second tissue contact areas respectively to first and second tissue sites comprises placing adhesive respectively between the first and second tissue contact areas and the first and second tissue sites.

39. The method of claim 37 where the steps of adhering the first and second tissue contact areas respectively to first and second tissue sites comprises mechanically attaching the first and second tissue contact areas respectively to the first and second tissue sites.

40. The method of claim 37 where the step of advancing the first tissue contact area towards the second tissue contact area comprises eroding a time-delay member comprising the bioerodible material associated with a support-providing member in such a way to tend to hold a spring attached to the first and second tissue contact areas in extension until the material has degraded.

41. The method of claim 37 where the bioerodible material comprises a support-providing member.

42. The method of claim 37 where the region to be supported comprises a surgically modified area.

43. A heart tissue supporting device comprising:
  a.) at least one first heart tissue adherence region and each adapted to adhere to selected first heart tissue regions on a heart surface,
  b.) at least one second heart tissue adherence region separated from the at least one first heart tissue adherence regions and each adapted to adhere to selected second heart tissue regions on a heart surface,
  c.) at least one heart support-providing member comprising at least one spring having opposed ends attached between the at least one first heart tissue adherence region and the at least one second heart tissue adherence region situated to maintain support to tissue between the at least one first heart tissue adherence region and the at least one second heart tissue adherence region, wherein each heart tissue adherence region is further adapted to be approximated towards one another along the heart surface and further comprising a time-delay member adapted to provide a period of time between an introduction of the heart tissue supporting member into a human body and initiation of a movement of the at least one first heart tissue adherence region towards the at least one second heart tissue adherence region.

44. The heart tissue supporting device of claim 43 where at least one of first heart tissue adherence regions and second heart tissue adherence regions is at least partially surrounded by a region that is substantially non adhering to heart tissue.

45. The heart tissue supporting device of claim 44 where the material forming at least a portion of the non adhering regions at least partially surrounding the at least one first heart tissue adherence region and the at least one second heart tissue adherence region is selected from the group consisting of woven or non-woven polymeric fabrics selected from the group consisting of polyfluorocarbons and polyolefins.

46. The heart tissue supporting device of claim 45 where the polyflurocarbons and polyolefins are selected from the group consisting of polytetrafluoroethylene (PTFE), ethylene chlorofluoroethylene (ECTFE), fluorinated ethylene propylene (FEP), polychlorotrifluoroethylene (PCTFE), polyvinylfluoride (PVF), polyvinylidenefluoride (PVDF), polyethylene (LDPE, LLDPE and HDPE), and polypropylene.

47. The heart tissue supporting device of claim 43 where the at least one support providing member is sized and placeable to maintain a first heart tissue contact region positioned against a second heart tissue contact region.

48. The heart tissue supporting device of claim 43 further including a connector strap that is substantially non adhering to heart tissue and is configured to connect the at least one first heart tissue adherence region and the at least one second heart tissue adherence region and thereby form, with the at least one support providing member, a loop adapted to surround a heart having the first and second heart tissue regions.

49. The heart tissue supporting device of claim 48 where the material forming at least a portion of the connector strap is selected from the group consisting of woven or non-woven polymeric fabrics selected from the group consisting of polyfluorocarbons and polyolefins.

50. The heart tissue supporting device of claim 49 where the polyfluorocarbons and polyolefins are selected from the group consisting of polytetrafluoroethylene (PTFE or TFE), ethylene chlorofluoroethylene (ECTFE), fluorinated ethylene propylene (FEP), polychlorotrifluoroethylene (PCTFE), polyvinylfluoride (PVF), polyvinylidenefluoride (PVDF), polyethylene (LDPE, LLDPE, and HDPE), and polypropylene.

51. The heart tissue supporting device of claim 43 where at least one of the first heart tissue adherence regions and the second heart tissue adherence regions comprises an adhering material selected to allow ingrowth of heart tissue into those regions.

52. The heart tissue supporting device of claim 51 where the adhering material is selected from the group consisting of woven or non-woven polymeric fabrics.

53. The heart tissue supporting device of claim 52 the woven or non-woven polymeric fabrics selected from polyethyleneterephthalate, cotton, and expanded polyfluorocarbons having internodal spacing suitable for intergrowth.

54. The heart tissue supporting device of claim 43 where the at least one spring comprises a coiled spring.

55. The heart tissue supporting device of claim 43 where the at least one spring comprises a flat spring.

56. The heart tissue supporting device of claim 43 where the time-delay member comprises a biodegradable material.

57. The heart tissue supporting device of claim 43 where the time-delay member is adapted to provide a period of time over which the distance between the at least one first heart tissue adherence region and the at least one second heart tissue adherence region varies.

58. The heart tissue supporting device of claim 57 where the time-delay member comprises a biodegradable material.

59. The heart tissue supporting device of claim 57 where the time-delay member is coated with a biodegradable material.

60. The heart tissue supporting device of claim 57 where the time-delay member is embedded in a biodegradable material.

61. The heart tissue supporting device of claim 57 where the time-delay member comprises a biodegradable material.

62. The heart tissue supporting device of claim 57 where the support providing member comprises a spring and the time-delay member comprises a biodegradable material member tending to hold the spring in extension until after functional biodegradation in the human body.

63. The heart tissue supporting device of claim 57 the time delay member is treated with at least one angiogenesis composition.

64. The heart tissue supporting device of claim 57 the time-delay member comprises at least one angiogenesis composition.

65. The heart tissue supporting device of claim 43 where at least of the one first heart tissue adherence region and the at least one second heart tissue adherence regions includes a surface selected to allow ingrowth of heart tissue into those regions.

66. The heart tissue supporting device of claim 65 where the surface is not smooth.

67. The heart tissue supporting device of claim 65 where the surface is roughened.

68. The heart tissue supporting device of claim 65 where the surface is nubbed.

69. The heart tissue supporting device of claim 65 where the surface is perforated.

70. The heart tissue supporting device of claim 65 where the surface is treated with at least one angiogenesis composition.

71. The heart tissue supporting device of claim 43 where at least a portion of the heart tissue supporting member is treated with at least one angiogenesis composition.

72. The heart tissue supporting device of claim 43 where at least one of the first heart tissue adherence region and second heart tissue adherence region support providing member are treated with at least one angiogenesis composition.

73. The heart tissue supporting device of claim 43 where at least of the one first heart tissue adherence region and the at least one second heart tissue adherence regions includes a mechanical fastener adapted to perforate heart tissue and cause adherence to those regions.

74. The heart tissue supporting device of claim 43 where at least of the one first heart tissue adherence region and the at least one second heart tissue adherence regions includes a surface including an adhesive selected to cause heart tissue adhesion onto those regions.

75. A method for providing support to a myocardial wall across an infarct, comprising:
   a.) at least one first heart tissue adherence region and each adapted to adhere to selected first heart tissue regions on a heart surface,
   b.) at least one second heart tissue adherence region separated from the at least one first heart tissue adherence regions and each adapted to adhere to selected second heart tissue regions on a heart surface,
   c.) at least one heart tissue support-providing member situated to maintain support to tissue between the at least one first heart tissue adherence region and the at least one second heart tissue adherence region, wherein each heart tissue adherence region is further adapted to be approximated towards one another along the heart surface, wherein at least a portion of the heart tissue support-providing member is treated with at least one angiogenesis compensation.

76. The heart tissue supporting device of claim 75 where at least one of first heart tissue adherence regions and second heart tissue adherence regions is at least partially surrounded by a region that is substantially non adhering to heart tissue.

77. The heart tissue supporting device of claim 76 where the material forming at least a portion of the non adhering regions at least partially surrounding the at least one first heart tissue adherence region and the at least one second heart tissue adherence region is selected from the group consisting of woven or non-woven polymeric fabrics selected from the group consisting of polyfluorocarbons and polyolefins.

78. The heart tissue supporting device of claim 77 where the polyflurocarbons and polyolefins are selected from the group consisting of polytetrafluoroethylene (PTFE), ethylene chlorofluoroethylene (ECTFE), fluorinated ethylene propylene (FEP), polychlorotrifluoroethylene (PCTFE), polyvinylfluoride (PVF), polyvinylidenefluoride (PVDF), polyethylene (LDPE, LLDPE and HDPE), and polypropylene.

79. The heart tissue supporting device of claim 75 where the at least one support providing member is sized and placeable to maintain a first heart tissue contact region positioned against a second heart tissue contact region.

80. The heart tissue supporting device of claim 75 further including a connector strap that is substantially non adhering to heart tissue and is configured to connect the at least one first heart tissue adherence region and the at least one second heart tissue adherence region and thereby form, with the at least one support providing member, a loop adapted to surround a heart having the first and second heart tissue regions.

81. The heart tissue supporting device of claim 80 where the material forming at least a portion of the connector strap is selected from the group consisting of woven or non-woven polymeric fabrics selected from the group consisting of polyfluorocarbons and polyolefins.

82. The heart tissue supporting device of claim 81 where the polyfluorocarbons and polyolefins are selected from the group consisting of polytetrafluoroethylene (PTFE or TFE), ethylene chlorofluoroethylene (ECTFE), fluorinated ethylene propylene (FEP), polychlorotrifluoroethylene (PCTFE), polyvinylfluoride (PVF), polyvinylidenefluoride (PVDF), polyethylene (LDPE, LLDPE, and HDPE), and polypropylene.

83. The heart tissue supporting device of claim 75 where at least one of the first heart tissue adherence regions and the second heart tissue adherence regions comprises an adhering material selected to allow ingrowth of heart tissue into those regions.

84. The heart tissue supporting device of claim 83 where the adhering material is selected from the group consisting of woven or non-woven polymeric fabrics.

85. The heart tissue supporting device of claim 84 where the woven or non-woven polymeric fabrics selected from polyethyleneterephthalate, cotton, and expanded polyfluorocarbons having internodal spacing suitable for intergrowth.

86. The heart tissue supporting device of claim 75 where the at least one support-providing member comprises at least one spring having opposing ends attached between the at least one first heart tissue adherence region and the at least one second heart tissue adherence region.

87. The heart tissue supporting device of claim 86 where the at least one spring comprises a coiled spring.

88. The heart tissue supporting device of claim 86 where the at least one spring comprises a flat spring.

89. The heart tissue supporting device of claim 86 where the support-providing member further comprises a time-delay member adapted to provide a period of time between an introduction of the heart tissue supporting member into a human body and initiation of a movement of the at least one first heart tissue adherence region towards the at least one second heart tissue adherence region.

90. The heart tissue supporting device of claim 89 where the time-delay member comprises a biodegradable material.

91. The heart tissue supporting device of claim 75 where the time-delay member is adapted to provide a period of time over which the distance between the at least one first heart tissue adherence region and the at least one second heart tissue adherence region varies.

92. The heart tissue supporting device of claim 91 where the time-delay member comprises a biodegradable material.

93. The heart tissue supporting device of claim 91 where the time-delay member is coated with a biodegradable material.

94. The heart tissue supporting device of claim 91 where the time-delay member is embedded in a biodegradable material.

95. The heart tissue supporting device of claim 91 where the time-delay member comprises a biodegradable material.

96. The heart tissue supporting device of claim 91 where the support providing member comprises a spring and the time-delay member comprises a biodegradable material member tending to hold the spring in extension until after functional biodegradation in the human body.

97. The heart tissue supporting device of claim 75 where at least of the one first heart tissue adherence region and the at least one second heart tissue adherence regions includes a surface selected to allow ingrowth of heart tissue into those regions.

98. The heart tissue supporting device of claim 97 where the surface is not smooth.

99. The heart tissue supporting device of claim 97 where the surface is roughened.

100. The heart tissue supporting device of claim 97 where the surface is nubbed.

101. The heart tissue supporting device of claim 97 where the surface is perforated.

102. The heart tissue supporting device of 97 where the surface is treated with at least one angiogenesis composition.

103. The heart tissue supporting device of claim 91 the time delay member is treated with at least one angiogenesis composition.

104. The heart tissue supporting device of claim 91 the time-delay member comprises at least one angiogenesis composition.

105. The heart tissue supporting device of claim 75 where at least one of the first heart tissue adherence region and second heart tissue adherence region support-providing member are treated with at least one angiogenesis composition.

106. The heart tissue supporting device of claim 75 where at least of the one first heart tissue adherence region and the at least one second heart tissue adherence regions includes a mechanical fastener adapted to perforate heart tissue and cause adherence to those regions.

107. The heart tissue supporting device of claim 75 where at least of the one first heart tissue adherence region and the at least one second heart tissue adherence regions includes a surface including an adhesive selected to cause heart tissue adhesion onto those regions.

* * * * *